(12) United States Patent
Ueda et al.

(10) Patent No.: US 7,034,539 B2
(45) Date of Patent: Apr. 25, 2006

(54) UNDERGROUND EXPLORATION APPARATUS, SYSTEM AND METHOD

(75) Inventors: Tomoaki Ueda, Kyoto (JP); Kazuhito Nakamura, Hyogo (JP); Yukio Kishimoto, Hyogo (JP); Naoya Ichimura, Kyoto (JP); Tokugen Yasuda, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/991,404

(22) Filed: Nov. 19, 2004

(65) Prior Publication Data

US 2005/0093548 A1  May 5, 2005

Related U.S. Application Data

(63) Continuation of application No. PCT/JP2004/010446, filed on Jul. 15, 2004.

(30) Foreign Application Priority Data

Jul. 16, 2003 (JP) ............................. 2003-197537

(51) Int. Cl.
*G01V 3/00* (2006.01)
(52) U.S. Cl. .................. 324/357; 324/347; 324/358
(58) Field of Classification Search ............. 324/347, 324/357, 358, 326–329; 702/12, 13
See application file for complete search history.

(56) References Cited

U.S. PATENT DOCUMENTS

| 1,808,397 | A | * | 6/1931 | Billotte et al. ............. 324/354 |
| 4,714,889 | A | * | 12/1987 | Chapman et al. ........... 324/366 |
| 6,373,254 | B1 | * | 4/2002 | Dion et al. ................. 324/369 |
| 6,765,386 | B1 | * | 7/2004 | Gianzero et al. ........... 324/367 |

FOREIGN PATENT DOCUMENTS

| JP | 52-801 B2 | 1/1977 |
| JP | 5-100044 | 4/1993 |
| JP | 6-94568 | 4/1994 |
| JP | 6-130156 | 5/1994 |
| JP | 7-012766 | 1/1995 |
| JP | 9-127253 | 5/1997 |
| JP | 9-127253 A | 5/1997 |
| JP | 10-293181 | 11/1998 |
| JP | 2883087 B2 | 2/1999 |
| JP | 2935229 B1 | 6/1999 |
| JP | 2000-019158 A | 1/2000 |
| JP | 2000-019159 A | 1/2000 |

(Continued)

*Primary Examiner*—Jay Patidar
(74) *Attorney, Agent, or Firm*—Fitzpatrick, Cella, Harper & Scinto

(57) ABSTRACT

The object of the present invention is to realize a low-invasive underground exploration apparatus, system, and method which are capable of specifying the kind, three-dimensional position, and amount of a substance present in the ground. The underground exploration apparatus, system, and method includes: measuring, at multiple points, a high frequency voltage that appears upon conduction of high frequency current through the ground to obtain measurement results at two or more frequency levels; employing an ground model using the finite element method, the boundary element method, an impedance network, or the like to estimate a substance in the ground by changing unknown quantities of the ground model such as local dielectric constant and electric conductivity so as to make an error between the actual measured value and the calculated value smaller; and displaying input information of the ground model and results of the estimation processing two-dimensionally or three-dimensionally.

15 Claims, 13 Drawing Sheets

FOREIGN PATENT DOCUMENTS

| | | |
|---|---|---|
| JP | 2000-028743 A | 1/2000 |
| JP | 2000-088691 A | 3/2000 |
| JP | 2000-258280 A | 9/2000 |
| JP | 2001-013111 A | 1/2001 |
| JP | 2001-074850 A | 3/2001 |
| JP | 2002-071822 A | 3/2002 |
| JP | 2002-156460 A | 5/2002 |
| JP | 2003-004686 A | 1/2003 |
| JP | 2003-004687 A | 1/2003 |
| WO | WO 2005/015262 A1 | 2/2005 |

\* cited by examiner

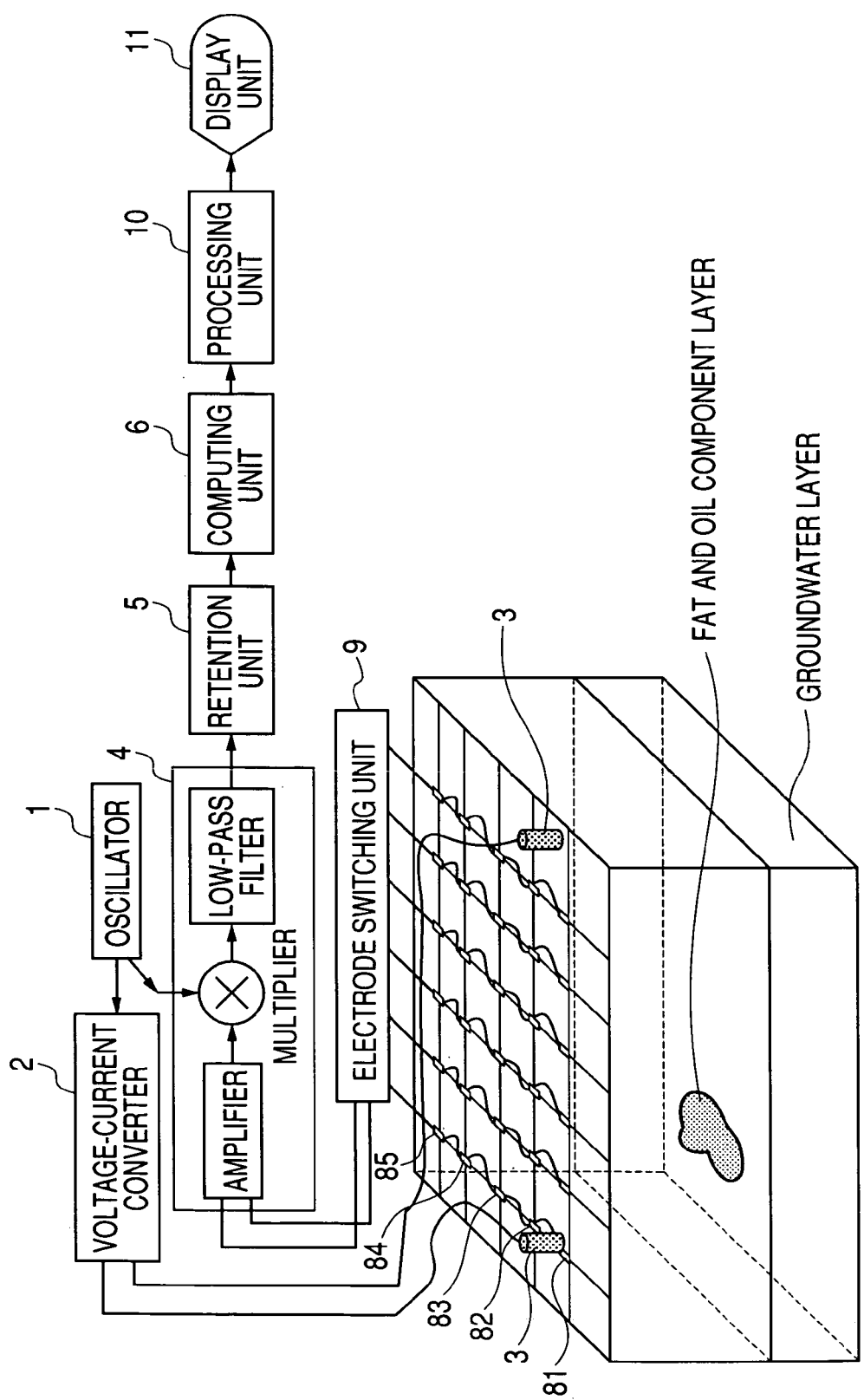

FIG. 2

| LIST | ABBREVIATION | DIELECTRIC CONSTANT | |
|---|---|---|---|
| AIR, GAS | | 1.000 | |
| WATER (PURE WATER) | | 55~85[mB] | 0°C |
| ALUMINA, SILICONE RUBBER, SODA GLASS | | 0~10 | |
| CRUDE OIL | | 1.0~2.5 | |
| SAND (DRY ⇒ CONTAINING WATER) | | 3~5 ⇒ 20~30 | |
| SOIL | | 5~40 | |
| TITANIUM OXIDE | | AROUND 100 | |
| BARIUM TITANIUM OXIDE | | SEVERAL THOUSANDS OR HIGHER | |
| 1, 1, 1-TRICHLOROETHANE | | 3.1 | 0°C |
| FLON 113 | | 2.4 | 25°C |
| FLUORINE-BASED AK-225 | | 4.1 | 25°C |
| METHYLENE CHLORIDE | | 9.1 | 20°C |
| ASAHI TRICHLOR | | 3.4 | 20°C |
| ASAHI PERCHLOR | | 2.4 | 15°C |
| POLYETHER ETHER KETONE | PEEK | 3.3 | at 1MHz |
| POLYETHER IMIDE | PEI | 3.15 | at 1MHz |
| POLYETHYLENE TEREPHTHALATE | PET | 3.2 | at 1MHz |
| POLYSULFONE | PSF | 3.05 | at 1KHz |
| POLYOXY BENZOYL | POB | 3.50 | at 1KHz |
| POLYETHERSULFONE | PES | 3.5 | at 1KHz |
| DAIFLON | 3F | 2.3~2.7 | at 1KHz |
| VINYLIDENE DIFLUORIDE | 2F | — | at 1KHz |
| ABS | ABS | 3.03 | at 1KHz |
| POLYPROPYLENE | PP | 1.0~2.3 | at 1KHz |
| POLYETHYLENE | PE | 2.3 | at 1KHz |
| ULTRA-HIGH MOLECULAR WEIGHT POLYETHYLENE | UPE | — | at 1KHz |
| POLYCARBONATE | PO | 2.94 | at 1KHz |
| NORYL | PPO | 2.60 | at 60Hz |
| POLYBUTYLENE TEREPHTHALATE | PBT | 3.5 | at 1KHz |
| POLYPHENYLENE SULFIDE 1G-40 ALMOST | PPS | 4 | at 1KHz |
| POLYAMIDE IMIDE | PAI | 3.5 | at 1KHz |
| POLYIMIDE | PI | 3.55 | at 60Hz |
| POLYOXYMETHYLENE (POLYACETAL) | POM | 3.7 | at 1KHz |
| MONOMER CAST NYLON | MO | 3.7 | at 1MHz |
| NYLON 6 (ABSOLUTELY DRY) | 6N | 3.0 | at 1KHz |
| NYLON 66 (ABSOLUTELY DRY) | 66N | 4 | at 1KHz |
| TEFLON | 4F | 2.6 | at 1KHz |

INTERFACE POLARIZATION

■ NO ELECTRIC FIELD  E=0          ■ ELECTRIC FIELD APPLIED  E≠0

● NEGATIVE CHARGE          ○ POSITIVE CHARGE

ORIENTATIONAL POLARIZATION

■ NO ELECTRIC FIELD  E=0          ■ ELECTRIC FIELD APPLIED  E≠0

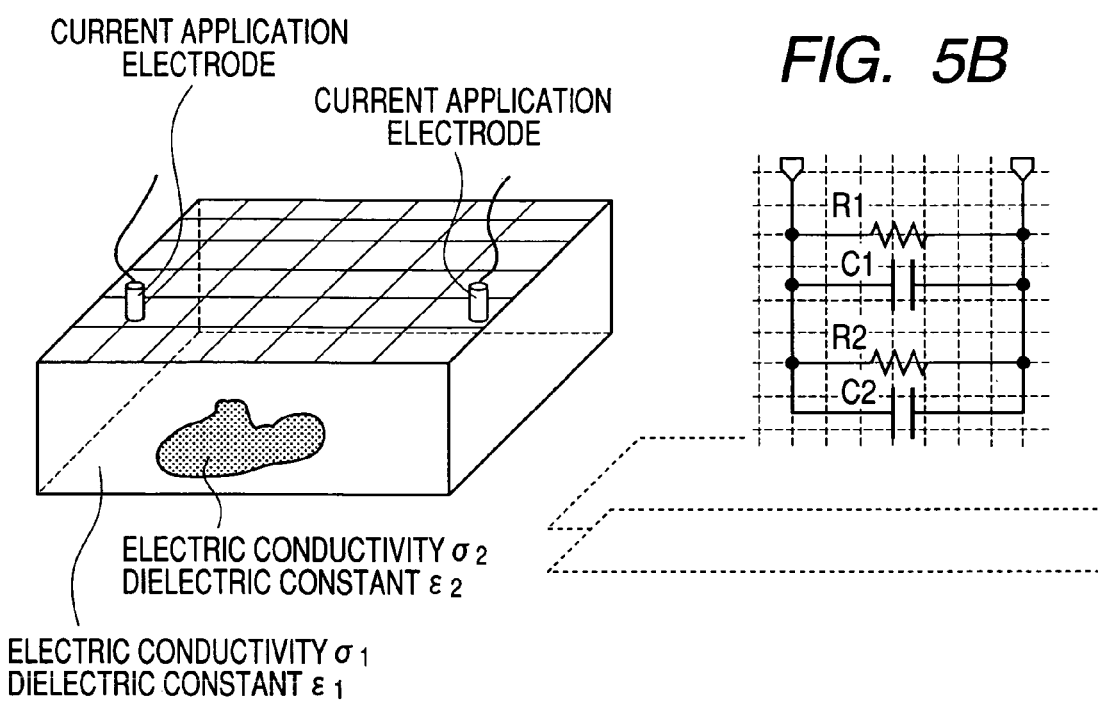
FIG. 5A
FIG. 5B
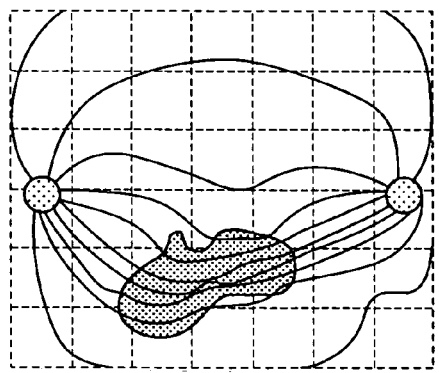
FREQUENCY $f_1$
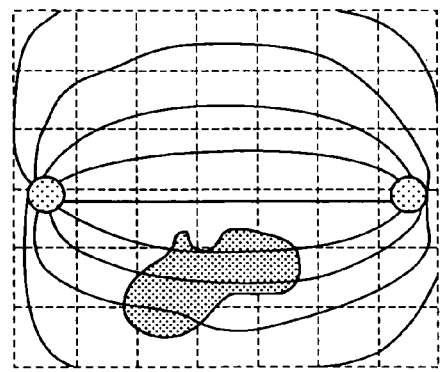
FREQUENCY $f_2$
FIG. 5C
FIG. 5D FREQUENCY $f_1$ FREQUENCY $f_2$ FREQUENCY $f_1-f_2$

⟷ MAJOR CURRENT COMPONENT

FREQUENCY $f_1-f_2$

⟷ $\left( \dfrac{\delta E}{\delta y} \quad \dfrac{-\delta E}{\delta x} \right)$

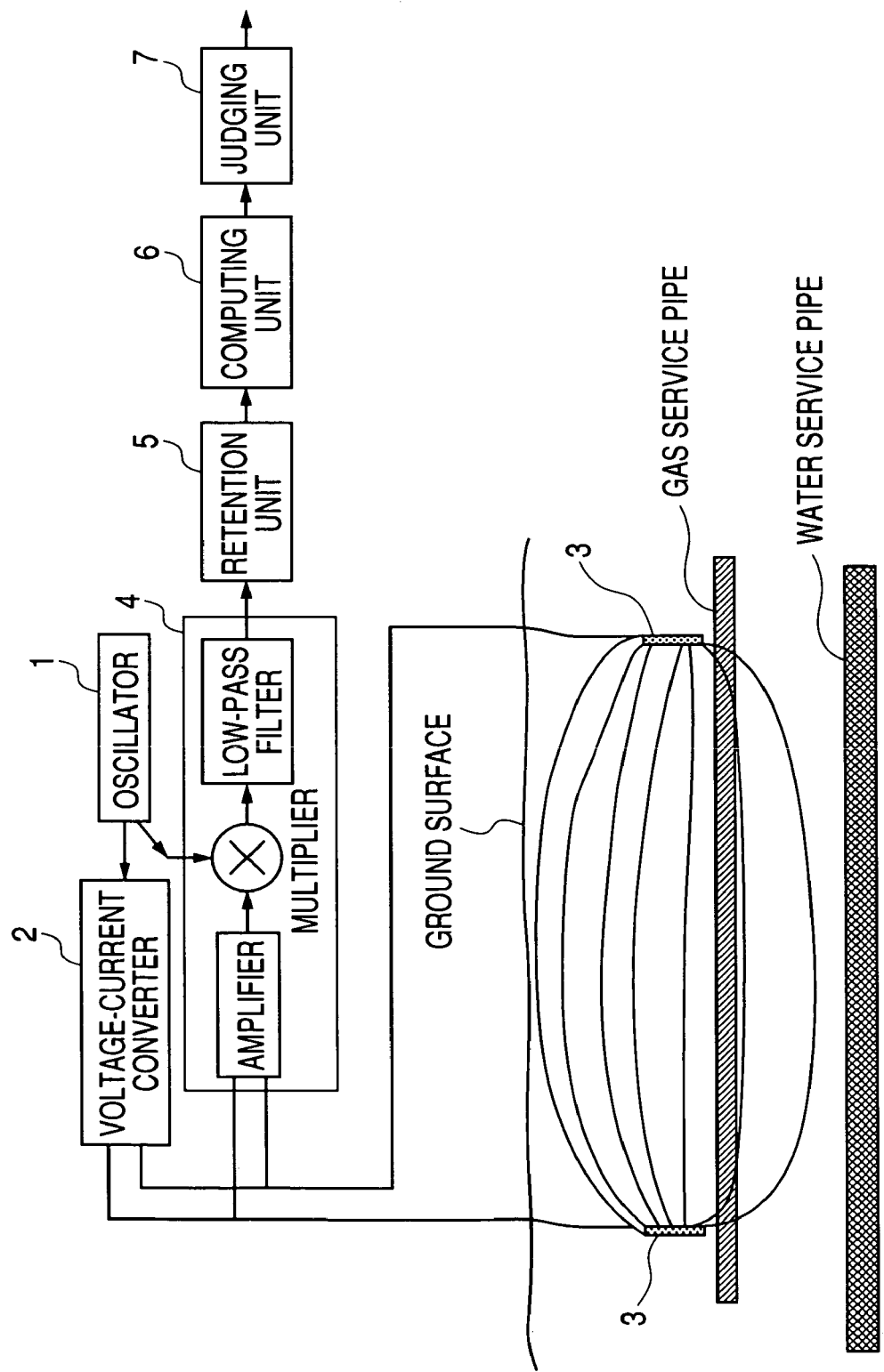

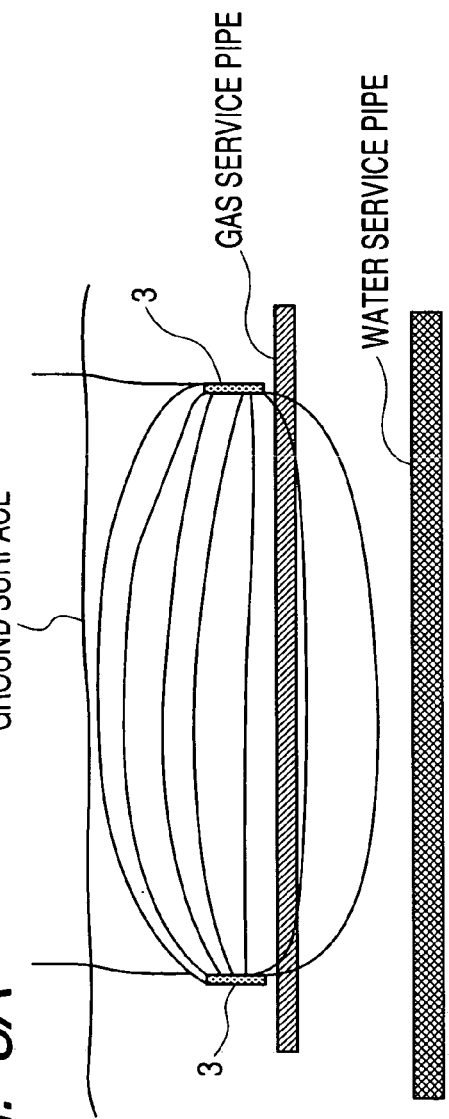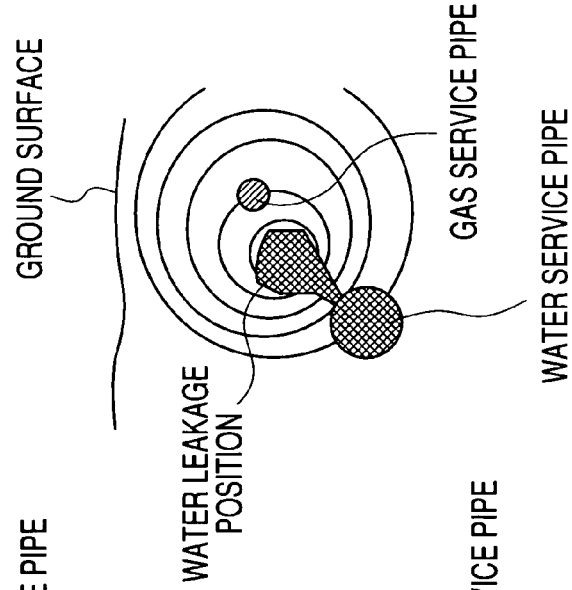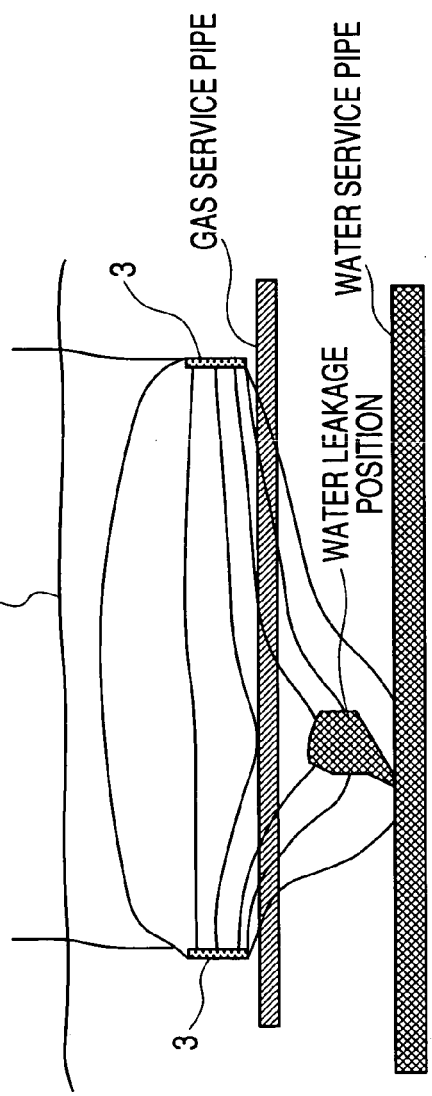

FIG. 11A  ▭─ ELECTRIC CONDUCTIVITY σ
              DIELECTRIC CONSTANT ε

UNDERGROUND EXPLORATION APPARATUS, SYSTEM AND METHOD

This application is a continuation of International Application No. PCT/JP2004/010446, filed Jul. 15, 2004, which claims the benefit of Japanese Patent Application No. 2003-197537 filed on Jul. 16, 2003.

BACKGROUND OF THE INVENTION

1. Field of the Invention

The present invention relates to a measurement apparatus which uses low-invasive, alternating current testing means to survey and observe the status of an underground water leakage, the location, geometry, depth, and amount of underground streams and resources or of soil contaminants, and the progress of soil improvement. More specifically, the present invention relates to an underground exploration apparatus which measures at multiple points a voltage generated by conducting electric current through the ground to obtain measurement results at two or more frequencies, which uses an ground model that employs the finite element method or the boundary element method, an impedance network, or the like, which changes an unknown quantity, such as the electric conductivity, dielectric constant per frequency, or position information, of a local area of the ground model so as to make the error between the actual measured value and the calculated value smaller, to thereby identify a substance under the ground or detect a change in geological condition, and which displays input information and estimation processing results of the ground model two-dimensionally or three-dimensionally.

2. Related Background Art

Conventional techniques of underground exploration include, in addition to a boring method of digging up portions of the ground as an invasive method, non-invasive methods. Known non-invasive underground exploration methods are 1) an acoustic exploration method of causing a local earthquake by artificially-induced vibration, 2) an X-ray backscattering method of photographing light backscattered from a highly conductive substance by irradiation of soft X-rays, 3) a underground radar exploration method of utilizing microwave irradiation, 4) an infrared photography method of taking a photograph of the near-infrared region from the sky, 5) a millimeter wave monitoring method of monitoring scattering millimeter waves from the sky, and so forth.

The acoustic exploration method of causing a local earthquake by artificially-induced vibration utilizes a phenomenon in which approximately no oscillatory waves are reflected in a region where the geological condition is homogenous and accordingly a substance density is substantially identical throughout the region, resulting in uniform acoustic impedance, whereas oscillatory waves are reflected at the border between different geological conditions where a substance density is varied and the acoustic impedance is discontinuous. By catching oscillatory waves reflected by a plane where the geological condition is discontinuous, this method can measure with precision the thickness and depth of a geological layer three-dimensionally and can visualize the measurements to display if the acoustic velocity is known for each geological layer's condition. A drawback of acoustic exploration is that the method cannot find an unknown substance in a geological layer where the density is approximately uniform and no oscillatory waves are reflected. In short, in the acoustic exploration method, it is possible to provide the depth and thickness of a geological layer, but it is not possible to find what substances the geological layer is made of unless a proper drilling survey is conducted. For instance, the acoustic exploration method is incapable of detecting the depth of an underground stream and the presence of underground resources or measuring whether or not the soil is contaminated by chemicals.

X-ray backscattering is a recently established underground exploration method of photographing light backscattered from a highly conductive substance by irradiation of soft X-rays. This method utilizes the nature of soft X-rays which possess properties of electromagnetic waves and particles both and which exhibit, owing to the skin effect of electromagnetic waves, excellent permeability in substances that are low in electric conductivity and magnetic permeability, substances with high dielectric constant, or substances that contain light atomic nuclei while exhibiting low permeability to be scattered or reflected against substances that are high in electric conductivity and magnetic permeability, substances with low dielectric constant, or substances that contain heavy atomic nuclei. This method is suitable for checking the presence or absence of a shallowly buried object, about several tens cm from the ground surface. A drawback of the X-ray backscattering method is to explore only areas near the ground surface when the soil has high water content. Another drawback of this method is that it is incapable of identifying the geological condition.

The underground radar exploration method using microwave irradiation can explore only a relatively shallow depth since the skin effect of electromagnetic waves prevent electromagnetic waves from entering the soil of high water content and causes electromagnetic waves to attenuate. This method cannot identify the geological condition, either.

The infrared photography method of taking a photograph of the near-infrared region from the sky catches near-infrared light radiated from the ground and is therefor suitable for gathering information related to temperature, for example, for detecting a region in the ground that is higher or lower in temperature than the surrounding areas. However, this method is incapable of identifying the kind and depth of a substance.

The millimeter wave monitoring method of monitoring scattering of millimeter waves from the sky is an exploration method that utilizes the nature of iron-rich soil to absorb millimeter waves, which enter the atmosphere from the Van Allen Belt surrounding the earth as a result of solar activity and are scattered above the ground. A drawback of this exploration method is that it is applicable only to geological surveys near the ground surface.

An example of other non-invasive, or only slightly-invasive, underground exploration methods is a method of measuring electric potential or electric conductivity by conducting current through the ground.

Listed below are results of conducting Gazette Text Search on the Industrial Property Digital Library website of Japan Patent Office by inputting the search terms "[Scope of Claim=or (underground, geological condition, exploration)] AND [Scope of Claim=and (current, electrode)".

The search found the following documents relating to techniques of detecting the location, point of corrosion, or site of coating damage of a buried pipe:

1) Japanese Patent Application Laid-Open No. 2002-071822, G01V 1/00, NOBUHIKO OYAMA, "POSITION DETECTING METHOD FOR BURIED PIPE";

2) Japanese Patent Application Laid-Open No. 2003-004686, G01N 27/20, SHINNIPPON STEEL Corp., "METHOD FOR DETECTING DAMAGED LOCATION

IN CORROSION-PROOF COATING OF EMBEDDED METAL PIPES USING INTEGRATING MEANS";

3) Japanese Patent Application Laid-Open No. 2003-004687, G01N 27/20, SHINNIPPON STEEL Corp., "METHOD FOR DETECTING DAMAGED LOCATION IN CORROSION-PROOF COATING OF EMBEDDED METAL PIPES USING TWO KINDS OF FREQUENCY SIGNALS";

4) Japanese Patent Application Laid-Open No. 2000-258280, G01M 3/18, FUJI ELECTRIC Corp., TAKESHI TAKASHIMA, "METHOD AND APPARATUS FOR DETECTING WATER LEAKAGE IN WATER SERVICE PIPE";

5) Japanese Patent Application Laid-Open No. 2001-013111, G01N 27/82, NIOPPN KOUKAN Corp., "PAINT FILM DAMAGED POSITION DETECTING METHOD AND APPARATUS OF BURIED COATED STEEL";

6) Japanese Patent Application Laid-Open No. 2000-019159, G01N 27/82, NIPPON KOUKAN Corp., "METHOD AND APPARATUS FOR DETECTING PAINT FILM DAMAGED POSITION OF BURIED STEEL PIPE";

7) Japanese Patent Application Laid-Open No. 2000-019158, G01N 27/82, NIPPON KOUKAN Corp., "METHOD AND APPARATUS FOR DETECTING PAINT FILM DAMAGED POSITION OF BURIED STEEL PIPE";

8) Japanese Patent Application Laid-Open No. 2000-088691, G01M 3/16, NISHIMATSU CONSTRUCTION Corp., "APPARATUS AND METHOD FOR MEASUREMENT OF LEAK OF WATER"; and 9) Japanese Patent Application Laid-Open No. H06-094568, G01M 3/40 7324-2G, MARUYAMA MANUFACTURER Co. Ltd., "METHOD AND APPARATUS FOR DETECTING LEAK OF WATER".

Document 1) relates to a method of using two electrodes and indirectly measuring the conductivity of direct current while varying measurement points. This method utilizes the fact that there is a change in distribution of current conduction when two measurement points sandwich a buried pipe. A drawback of this method is that the result is easily influenced by water content, the diameter, direction, kind, and depth of the buried pipe, and other objects embedded in the ground. Documents 2), 3), 4), 5), 6), and 7) relate to a method of using a buried metal pipe as one of current application electrodes. Document 8) relates to a direct measurement method which utilizes the fact that a water leakage taking place on an array of pre-arranged electrodes causes a change in interelectrode impedance. Document 9) relates to an indirect measurement method which utilizes the fact that an electric resistivity between the soil portions of both side of a water channel is changed when the channel is closed and when the channel is opened.

The search found the following documents as prior art relating to geological surveys that use AC tests:

10) Japanese Patent Application Laid-Open No. H10-293181, G01V 3/06, OYO CHISHITSU Corp., "MULTI-CHANNEL ELECTRIC SURVEY METHOD WITH CAPACITOR METHOD";

11) Japanese Patent Application Laid-Open No. 2001-074850, G01V 3/08, OYO CHISHITSU Corp., "ELECTRIC SURVEYING METHOD USING NON-POLARIZING ELECTRODE";

12) Japanese Patent Application Laid-Open No. H09-127253, G01V 3/08, OYO CHISHITSU Corp., "MULTI-CHANNEL ELECTRIC SEARCHING SYSTEM EMPLOYING CAPACITOR METHOD";

13) Japanese Patent Application Laid-Open No. 2002-156460, G01V 3/02, TLO KYUSHU Corp., LTD: KK "ELECTRIC SEARCHING METHOD, ELECTRIC SEARCHING APPARATUS USING THE SAME, AND LAND MINE DETECTING APPARATUS";

14) Japanese Patent Application Laid-Open No. 2000-028743, G01V 3/12, MITSUI ENGINEERING & SHIPBUILD Corp., "BURIED OBJECT PROSPECTING METHOD AND NON-CONTACT HIGH-FREQUENCY CURRENT SENSOR FOR DETECTING CAVITY"; and 15) Japanese Patent Application Laid-Open No. H07-012766, G01N 27/00 D 9115-2J, KAJIMA CONSTRUCTION Corp., "UNDERGROUND FLOW CHARACTERISTIC MEASURING METHOD AND APPARATUS USING SPECIFIC RESISTANCE".

Document 10) relates to a method of measuring direct current specific resistance with precision by employing a general AC test method to correct the influence of frequency and distance attenuation. Document 11) relates to a method of measuring the charging ratio and direct current specific resistance of electrodes by a general AC test method. Document 12) shows an embodiment of a system of measuring specific resistance by an AC test. Document 13) relates to an apparatus for detecting the presence or absence of a buried object immediately below a current electrode for measurement by measuring the electric potential of areas surrounding the current electrode for measurement while limiting current paths by providing an infinite distance current electrode and while changing the position of the current electrode for measurement. Document 14) relates to a method of measuring electric conductivity by an AC test. Document 15) relates to a method which uses an AC test together with tracer fluid injection.

The signal tracing method is included in the AC test method but uses a detector of the same resonance frequency as the applied frequency instead of measuring electric potential. In the search, the identified literature on the signal tracing method consisted of the following document:

16) Japanese Patent Application Laid-Open No. H06-130156, G01V 3/08 B 7256-2G, NIPPON TELEGRAPH & TELEPHONE Corp., "METHOD AND APPARATUS FOR SEARCHING EMBEDDED METAL".

The following was found in the search as a document on an apparatus which uses a current path contrived to obtain specific resistance by numerical calculation and which displays a tomographic image:

17) Japanese Patent Application Laid-Open No. H05-100044, G01V 3/02 C 7256-2G, DIA CONSULTANT Corp., "AUTOMATIC ELECTRIC PROBING METHOD".

Although the status of water leakage from a water service pipe buried under the ground can be detected even by development in the above prior art, those techniques cannot detect occurrence of the phenomenon called "sandblast" (a blast of soil and sand mixed with a water stream) which accompanies, for example, water leakage from a water service pipe buried in the vicinity of an embedded gas service pipe toward the gas service pipe, or a rapid water leakage.

In addition, the above prior art is capable of detecting how specific resistance (electric conductivity) is distributed but not of specifying the location, depth, and amount of underground streams and resources or soil contaminants, and substances contained in a geological layer, nor measuring or monitoring the progress of soil improvement since the electric conductivity is hardly changed by a change in frequency.

An object of the present invention is to provide a low-invasive technique of exploring under the ground using a low-invasive AC test method. More specifically, an object of the present invention is to provide a technical measure capable of specifying the location, depth, and amount of underground streams and resources or soil contaminants, and substances contained in a geological layer, or measuring or monitoring the progress of soil improvement.

Another object of the present invention is to provide a method of conducting an AC test without allowing AC noise, such as that caused by an electric current fed back or leaked to the ground from a power transmission line or from the overhead wire of a railway, to influence the test.

Still another object of the present invention is to detect the sandblast phenomenon caused by water leakage from a water service pipe that is buried in the vicinity of a gas service pipe.

SUMMARY OF THE INVENTION

According to a first aspect of the present invention, there is provided an underground exploration apparatus including: an oscillator capable of selecting among two or more fundamental oscillation frequencies; a voltage-current converter for converting a voltage signal generated by the oscillator into current; a pair of electrodes placed on or buried in the ground apart from each other in order to conduct a high frequency current supplied by the voltage-current converter through the ground; a measuring unit for measuring a high frequency voltage generated between ends of the electrodes to detect an impedance between two points of the electrodes; a retention unit for holding a value of the impedance outputted from the measuring unit for each oscillation frequency; a computing unit for calculating a difference between impedances held by the retention unit to obtain an impedance difference resulting from different oscillation frequencies; and a judging unit for detecting and judging a large change in impedance between the two points of the electrodes within a short time by at least one of the frequencies, based on the impedance difference calculated by the computing unit.

According to a second aspect of the present invention, there is provided an underground exploration apparatus including: an oscillator capable of selecting among two or more fundamental oscillation frequencies; a voltage-current converter for converting a voltage signal generated by the oscillator into current; a pair of current application electrodes placed on or buried in the ground apart from each other in order to conduct a high frequency current supplied by the voltage-current converter through the ground; a pair of voltage measurement electrodes placed apart from each other at positions different from locations where the current application electrodes are set; a measuring unit for measuring a high frequency voltage generated between the two voltage measurement electrodes to detect an impedance between two points of the electrodes; a retention unit for holding a value of the impedance outputted from the measuring unit for each oscillation frequency; and a computing unit for calculating an impedance difference resulting from different applied oscillation frequencies, based on the impedance values held by the retention unit.

According to a third aspect of the present invention, there is provided an underground exploration apparatus including: an oscillator capable of selecting among two or more fundamental oscillation frequencies; a voltage-current converter for converting a voltage signal generated by the oscillator into current; a pair of current application electrodes placed on or buried in the ground apart from each other in order to conduct a high frequency current supplied by the voltage-current converter through the ground; N voltage measurement electrodes, N being 2 or more, placed apart from one another at positions different from locations where the current application electrodes are set; an electrode switching unit for selecting an arbitrary pair of voltage measurement electrodes from the N voltage measurement electrodes and supplying voltage to the selected pair of the electrodes; a measuring unit for measuring a high frequency voltage generated between the two electrodes selected by the electrode switching unit to detect an impedance between two points of the selected electrodes; a retention unit for holding a value of the impedance outputted from the measuring unit for each oscillation frequency; and a computing unit for calculating an impedance difference resulting from different applied oscillation frequencies, based on the impedance values held by the retention unit.

According to a fourth aspect of the present invention, there is provided an underground exploration apparatus including: an oscillator capable of selecting among two or more fundamental oscillation frequencies; a voltage-current converter for converting a voltage signal generated by the oscillator into current; M current application electrodes, M being 2 or more, placed on or buried in the ground apart from one another in order to conduct a high frequency current through the ground; a current supply selecting unit for selecting an arbitrary pair of current application electrodes from the current application electrodes and supplying a current outputted from the voltage-current converter; N voltage measurement electrodes, N being 2 or more, placed apart from one another at positions different from locations where the current application electrodes are set; an electrode switching unit for selecting, an arbitrary pair of voltage measurement electrodes from the N voltage measurement electrodes and supplying voltage to the selected pair of the electrodes; a measuring unit for measuring a high frequency voltage generated between the two electrodes selected by the electrode switching unit to detect an impedance between two points of the selected electrodes; a retention unit for holding a value of the impedance outputted from the measuring unit for each oscillation frequency; and a computing unit for calculating an impedance difference resulting from different applied oscillation frequencies, based on the impedance value held by the retention unit.

In the underground exploration apparatus according to the first to fourth aspects of the present invention, preferably the voltage signal generated by the oscillator is a sine wave, a triangular wave, a saw tooth wave, or a rectangular wave, or one obtained by diphase modulation of the sine wave, triangular wave, saw tooth wave, or rectangular wave with a maximum length binary code sequence of a frequency that corresponds to the quotient of the fundamental oscillation frequency divided by an integer.

The underground exploration apparatus according to the second aspect of the present invention preferably further includes a mechanism for moving the pair of voltage measurement electrodes on a ground surface with a distance between the electrodes kept to a fixed value, wherein measurement is carried out while the voltage measurement electrodes are moved on the ground surface.

In the underground exploration apparatus according to the third and fourth aspects of the present invention, the N voltage measurement electrodes are preferably arranged two-dimensionally on a ground surface, and a display unit is preferably provided which displays two-dimensional map based on data, supplied from the computing unit, of the impedance difference resulting from the different applied oscillation frequencies.

In the underground exploration apparatus according to the third and fourth aspects of the present invention, preferably the N voltage measurement electrodes are arranged two-dimensionally on a ground surface, and a display unit is provided which performs two-dimensional interpolation processing based on data supplied, from the computing unit, of the impedance difference resulting from the different applied oscillation frequencies, deems the two-dimensional arrangement as a plane with respect to the obtained two-dimensional interpolation values, and performs differentiation processing in each direction of two axes of x and y on the plane where the axis x and the axis y intersect each other, and displays a two-dimensional vector or arrow map by deeming an x-directional differential value and a y-directional differential value as components of a vector.

In the above-mentioned underground exploration apparatus, preferably a processing unit is provided which solves a forward problem of an applied current based on three-dimensional coordinates of the M current application electrodes and the N voltage measurement electrodes and ground data by using a finite element method or a boundary element method, or by using an impedance network, to obtain a high frequency voltage amplitude value that appears in the voltage measurement electrodes in a ground model, and to estimate a substance in the ground by changing the local dielectric constant and electric conductivity of the ground model so as to make an error between the actual measured value and the calculated value smaller, and a display unit is provided which performs two-dimensional or three-dimensional display processing upon receiving input information and the results of the estimation processing from the processing unit.

According to a fifth aspect of the present invention, there is provided an underground exploration system including: an oscillator capable of selecting among two or more fundamental oscillation frequencies; a voltage-current converter for converting a voltage signal generated by the oscillator into current; a pair of electrodes placed on or buried in the ground apart from each other in order to conduct a current supplied by the voltage-current converter through the ground; a measuring unit for measuring a voltage generated between both ends of the electrodes to detect an impedance between two points of the electrodes; a retention unit for holding a value of the impedance outputted from the measuring unit for each oscillation frequency; a computing unit for calculating a difference between impedances held by the retention unit to obtain an impedance difference resulting from different oscillation frequencies; and a judging unit for detecting and judging from the impedance difference calculated by the computing unit that there is a great change in impedance between the two points of the electrodes within a short period of time at one, or more, of the frequencies.

According to a sixth aspect of the present invention, there is provided an underground exploration system including: an oscillator capable of selecting among two or more fundamental oscillation frequencies; a voltage-current converter for converting a voltage signal generated by the oscillator into current; a pair of current application electrodes placed on or buried in the ground apart from each other in order to conduct a current supplied by the voltage-current converter through the ground; a pair of voltage measurement electrodes placed apart from each other at positions different from the locations of the current application electrodes; a measuring unit for measuring a voltage generated between the two voltage measurement electrodes to detect an impedance between two points of the electrodes; a retention unit for holding a value of the impedance outputted from the measuring unit for each oscillation frequency; and a computing unit for calculating an impedance difference resulting from different applied oscillation frequencies, based on the impedance values held by the retention unit.

According to a seventh aspect of the present invention, there is provided an underground exploration system including: an oscillator capable of selecting among two or more fundamental oscillation frequencies; a voltage-current converter for converting a voltage signal generated by the oscillator into current; a pair of current application electrodes placed on or buried in the ground apart from each other in order to conduct a current supplied by the voltage-current converter through the ground; N voltage measurement electrodes, N being 2 or more, placed apart from one another at positions different from the locations of the current application electrodes; an electrode switching unit for selecting an arbitrary pair of voltage measurement electrodes from the N voltage measurement electrodes and supplying voltage to the selected pair of the electrodes; a measuring unit for measuring a voltage generated between the two electrodes selected by the electrode switching unit to detect an impedance between two points of the selected electrodes; a retention unit for holding a value of the impedance outputted from the measuring unit for each oscillation frequency; and a computing unit for calculating an impedance difference resulting from different applied oscillation frequencies, based on the impedance values held by the retention unit.

According to an eighth aspect of the present invention, there is provided an underground exploration system including: an oscillator capable of selecting among two or more fundamental oscillation frequencies; a voltage-current converter for converting a voltage signal generated by the oscillator into current; M current application electrodes, M being 2 or more, placed on or buried in the ground apart from one another in order to conduct a current through the ground; a current supply selecting unit for selecting an arbitrary pair of current application electrodes from among the M current application electrodes and supplying a current outputted from the voltage-current converter to the selected pair of the electrodes; N voltage measurement electrodes, N being 2 or more, placed apart from one another at positions different from the locations of the M current application electrodes; an electrode switching unit for selecting an arbitrary pair of voltage measurement electrodes from the N voltage measurement electrodes and supplying voltage to the selected pair of the electrodes; a measuring unit for measuring a voltage generated between the two electrodes selected by the electrode switching unit to detect an impedance between two points of the selected electrodes; a retention unit for holding a value of the impedance outputted from the measuring unit for each oscillation frequency; and a computing unit for calculating an impedance difference resulting from different applied oscillation frequencies, based on the impedance values held by the retention unit.

According to a ninth aspect of the present invention, there is provided an underground exploration method including: a step of conducting a current of two or more different oscillation frequencies through a pair of current application electrodes placed on or buried in the ground apart from each other, or an arbitrary pair of current application electrodes selected from a plurality of current application electrodes placed on or buried in the ground apart from one another; a step of measuring a voltage generated between a pair of voltage measurement electrodes placed on the ground apart from each other, or between an arbitrary pair of voltage measurement electrodes selected from a plurality of voltage measurement electrodes placed on the ground apart from one another to detect an impedance between two points of the pair of voltage measurement electrodes; a step of holding the impedance values for each oscillation frequency; and a step of calculating a difference in the impedance value to obtain an impedance difference resulting from different oscillation frequencies.

Preferably, the underground exploration method according to the ninth aspect of the present invention further includes a step of detecting and judging that the impedance difference is changed.

BRIEF DESCRIPTION OF THE DRAWINGS

FIG. 1 is a diagram illustrating the structure of an underground exploration apparatus according to an embodiment of the present invention (Embodiment 3);

FIG. 2 is a table showing that different soil substances as well as different chemicals have different specific dielectric constants;

FIGS. 5A, 5B, 5C and 5D are diagrams illustrating the change of a current path which is caused by a local difference in geological condition deep under the ground due to a change in dielectric constant dependent on the frequency of an applied current;

FIG. 7 is a diagram illustrating the structure of an underground exploration apparatus according to an embodiment of the present invention (Embodiment 1);

FIGS. 8A, 8B and 8C are diagrams illustrating the principle of operation of detecting a sandblast phenomenon, which accompanies water leakage, according to an embodiment of the present invention (Embodiment 1);

FIGS. 11A and 11B are diagrams illustrating an example of a ground model for an underground exploration apparatus according to an embodiment of the present invention (Embodiment 3);

DETAILED DESCRIPTION OF THE PREFERRED EMBODIMENTS

Tomoaki Ueda, one of the inventors, has found as a result of extensive research that the dielectric constant $\epsilon$ of geological constituents and soil contaminants constituting the ground, and groundwater is greatly changed depending on the frequency of a current applied and the capacitance C which is distributed is also greatly changed, whereas the electric conductivity a thereof is hardly changed.

Figure 3:
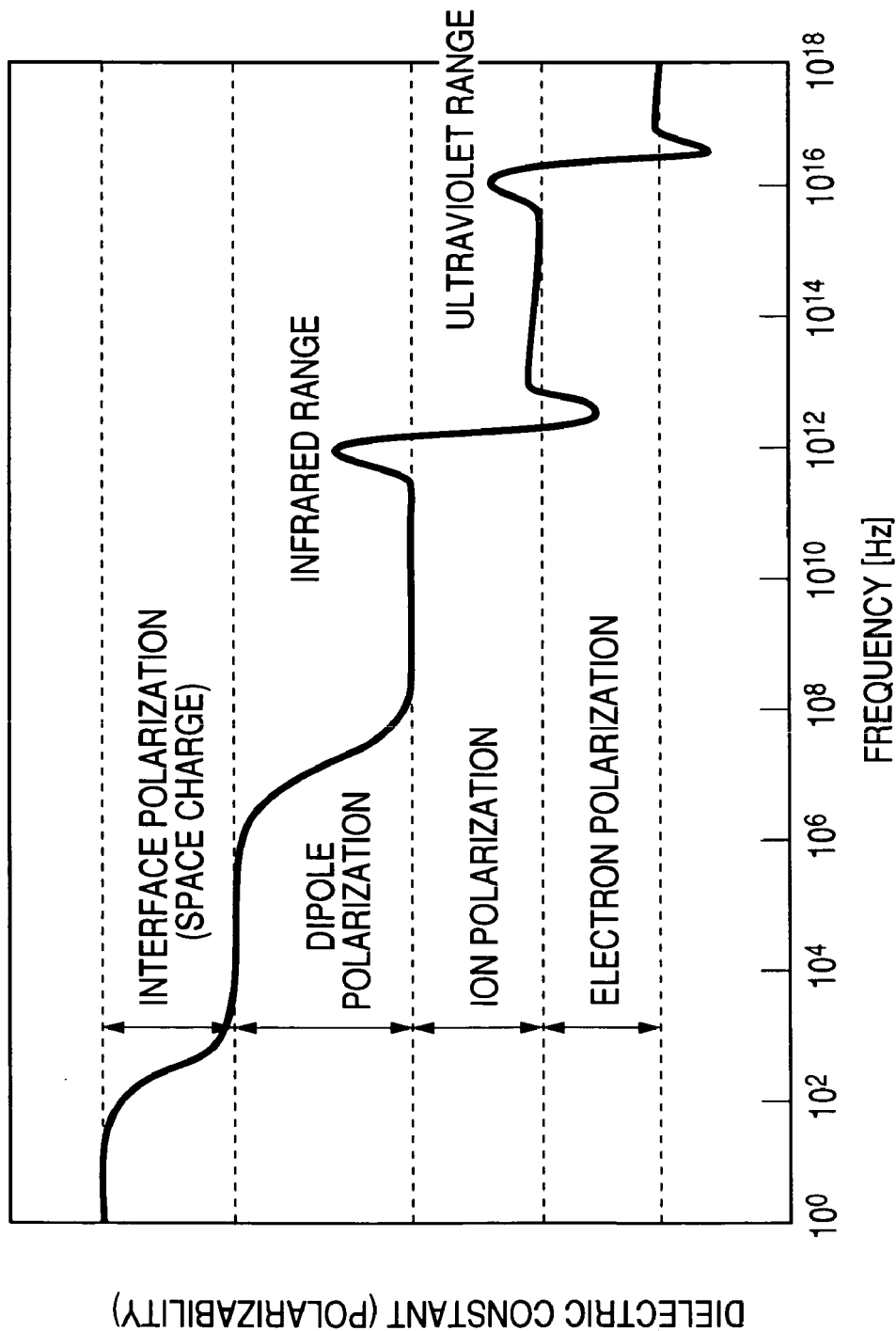
FIG. 3 is a diagram illustrating the frequency dependency of dielectric constant, and the factors for the dependency.

It is a known fact that different substances have different specific dielectric constants as shown in FIG. 2. Specific dielectric constant is the ratio of the material's dielectric constant to the dielectric constant of a vacuum. The dielectric constant is known to have frequency dependency, as shown in FIG. 3. Substances that are more readily polarized have larger dielectric constants. The known types of polarization and their causes are 1) interface polarization accompanying migration of space charges, 2) dipole polarization related to polarization of molecules or particles that constitute a substance, 3) ion polarization due to migration of atomic nuclei, and 4) electronic polarization due to migration of electrons.

Figure 4A:
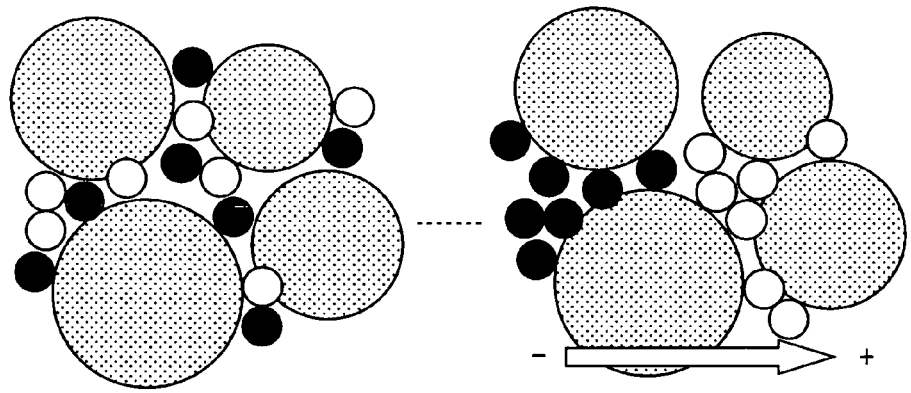
FIGS. 4A and 4B are diagrams illustrating interface polarization and orientational polarization, respectively.
Figure 4B:
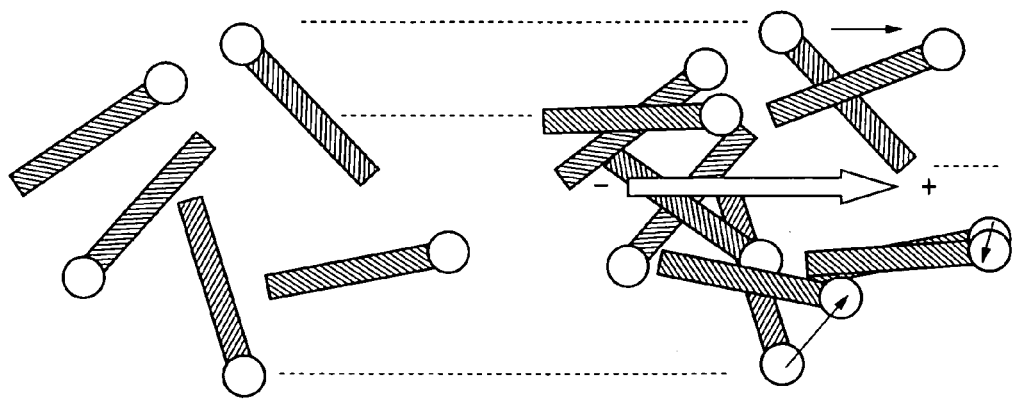

Two of the above polarization types, interface polarization and dipole polarization, are shown in FIGS. 4A and 4B, respectively. Interface polarization is a phenomenon in which charged particles are moved through gaps between particles by an externally applied electric field. Therefore, interface polarization is considered to depend greatly on the grain size and properties of the soil, sand and stones that constitute the ground, and it is a known fact that a change in dielectric constant dependent on interface polarization is prominent at a frequency between DC and a few kHz. Dipole polarization is a phenomenon caused when molecule orientation is aligned in the same direction by an externally applied electric field, and is considered to depend greatly on rotation of molecules and particles of substances contained in a geological layer which is induced by moment given upon application of an electric field.

Therefore, a substance can be identified by conducting an AC test at two or more frequencies selected appropriately for the frequency of an applied current since change of the dielectric constant depending on geological substances or substances contained in the ground makes frequencies different. That is the point Tomoaki Ueda, one of the inventors of the present invention, has focused his attention on.

An underground exploration apparatus according to the present invention comprises an oscillator 1 capable of selecting among two or more fundamental oscillation frequencies; a voltage-current converter 2 for converting a voltage signal generated by the oscillator 1 into current; a pair of electrodes 3 placed on or buried in the ground apart from each other in order to conduct a high frequency current supplied by the voltage-current converter 2 through the ground; a measuring unit 4 for measuring a high frequency voltage generated between the ends of the electrodes 3 to detect the impedance between two points of the electrodes; a retention unit 5 for holding the impedance value outputted from the measuring unit 4 for each oscillation frequency; a computing unit 6 for calculating a difference between impedances held by the retention unit 5 to obtain an impedance difference resulting from different oscillation frequencies; and a judging unit 7 for detecting and judging a large change in impedance between the two points of the electrodes 3 within a short time at least one of the frequencies, based on the impedance difference calculated by the computing unit 6. The electric conductivity of the electrodes is very low compared to the electric conductivity of substances that constitute the ground, and therefore the two-terminal method is sufficient for accurate impedance measurement. From the difference between impedances thus measured at a plurality of frequencies, a change in dielectric constant can be caught with precision making it possible to detect a change in the ground which takes place in the vicinity of the shortest current path between the pair of electrodes 3.

The pair of electrodes 3 is preferably positioned near a buried gas service pipe. This makes it possible correctly to detect, from a change in dielectric constant of the soil in the water leakage area, a sign of the sandblast phenomenon, which accompanies a water leakage from a water service pipe buried in the vicinity of the shortest current path between the electrodes 3 and which could influence maintenance of the gas service pipe seriously. This is based on the fact that AC current is inclined to flow in the water leakage area, since the specific dielectric constant of water is about 80, whereas soil generally has a specific dielectric constant of 5 to 40.

Preferably, the frequency applied is set to 1 kHz to 10 MHz, and application of direct current is avoided. This makes it possible to prevent a corrosion current which causes corrosion from flowing when a coating of the gas service pipe is defective, and the apparatus can catch a large change in impedance even with a weak current.

An underground exploration apparatus according to another aspect of the present invention comprises an oscillator 1 capable of selecting among two or more fundamental oscillation frequencies; a voltage-current converter 2 for converting a voltage signal generated by the oscillator 1 into current; a pair of current application electrodes 3 placed on or buried in the ground apart from each other in order to conduct a high frequency current supplied by the voltage-current converter 2 through the ground; a pair of voltage measurement electrodes 81 and 82 placed apart from each other at positions different from the locations where the current application electrodes 3 are set; a measuring unit 4 for measuring a high frequency voltage generated between the two voltage measurement electrodes 81 and 82 to detect the impedance between two points of the electrodes; a retention unit 5 for holding the impedance value outputted from the measuring unit 4 for each oscillation frequency; and a computing unit 6 for calculating an impedance difference resulting from different applied oscillation frequencies, based on the impedance values held by the retention unit 5. This underground exploration apparatus is capable of searching for a point on the ground surface where the impedance sharply changes by carry out measurement while moving the voltage measurement electrodes 81 and 82 from one measurement point to another on the ground surface.

An underground exploration apparatus according to still another aspect of the present invention comprises an oscillator 1 capable of selecting among two or more fundamental oscillation frequencies; a voltage-current converter 2 for converting a voltage signal generated by the oscillator 1 into current; a pair of current application electrodes 3 placed on or buried in the ground apart from each other in order to conduct a high frequency current supplied by the voltage-current converter 2 through the ground; voltage measurement electrodes 81, 82, . . . 8N, in a total number of N being 2 or more, placed apart from one another at positions different from locations where the current application electrodes 3 are set; an electrode switching unit 9 for selecting an arbitrary pair of voltage measurement electrodes from voltage measurement electrodes 81, 82, . . . 8N, in a total number of N being 2 or more, and supplying voltage to the selected pair of the electrodes; a measuring unit 4 for measuring a high frequency voltage generated between the two electrodes selected by the electrode switching unit 9 to detect the impedance between two points of the selected electrodes; a retention unit 5 for holding a value of the impedance outputted from the measuring unit 4 for each oscillation frequency; and a computing unit 6 for calculating an impedance difference resulting from different applied oscillation frequencies, based on the impedance values held by the retention unit 5. This underground exploration apparatus is capable of underground exploration deep in the ground as well as near the ground surface through an electric potential observation conducted on the ground surface. This means that the apparatus is capable of identifying the location, depth and amount of underground streams and resources or soil contaminants, and substances contained in a geological layer, or measuring or monitoring the progress of soil improvement.

Figure 13A:
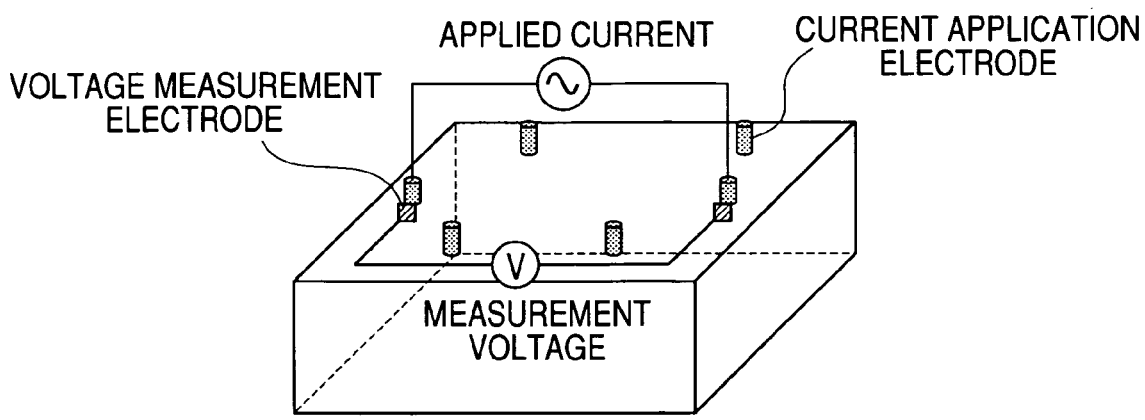
FIGS. 13A, 13B and 13C are diagrams illustrating the structure of an underground exploration apparatus according to an embodiment of the present invention.
Figure 13B:
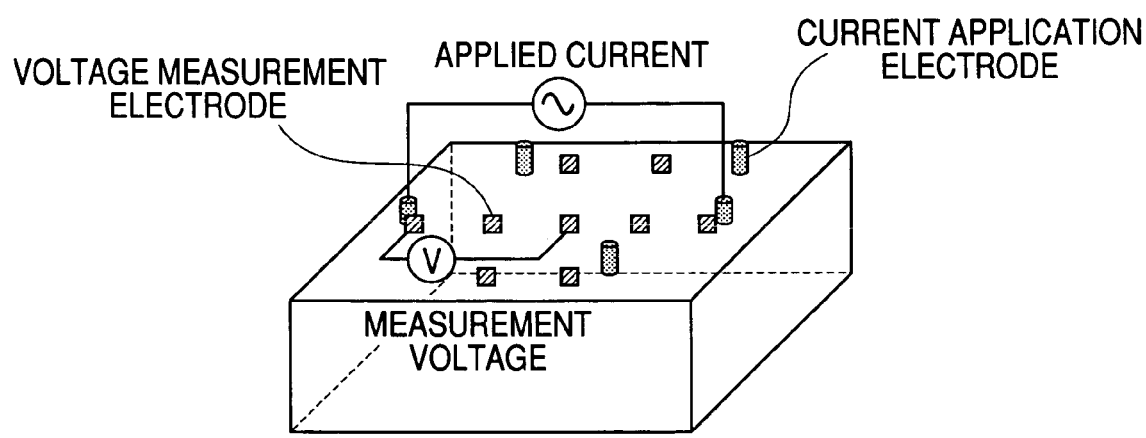
Figure 13C:
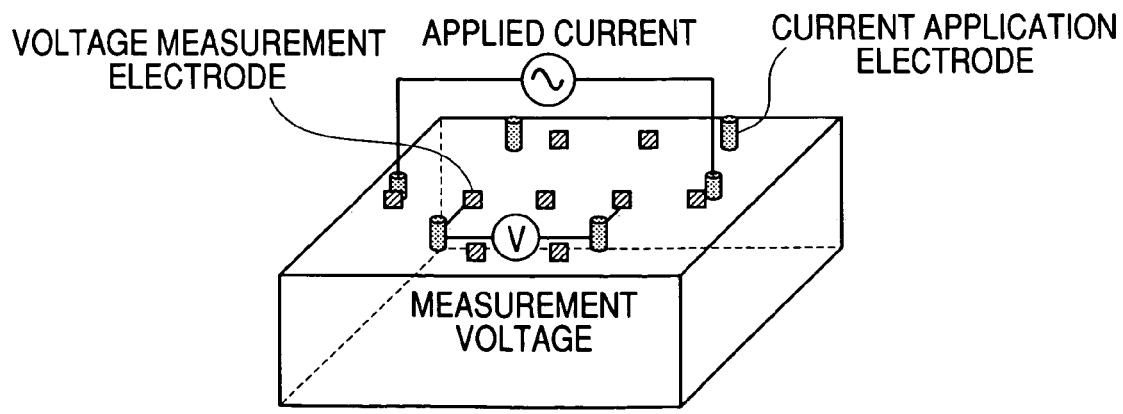

The voltage measurement electrodes 81, 82, . . . 8N are preferably arranged on a two-dimensional, net-like sheet, so that electric potential measurement points can be mapped out on the ground with ease by spreading the net-like sheet over the ground. The voltage measurement electrodes may be integral with the current application electrodes as shown in FIGS. 13A and 13B, or may be separate from the current application electrodes, as shown in FIG. 13C.

An underground exploration apparatus according to yet another aspect of the present invention comprises an oscillator 1 capable of selecting among two or more fundamental oscillation frequencies; a voltage-current converter 2 for converting a voltage signal generated by the oscillator 1 into current; M current application electrodes 31, 32, . . . 3M, M being 2 or more, placed on or buried in the ground apart from one another in order to conduct a high frequency current through the ground; a current supply selecting unit 12 for selecting an arbitrary pair of current application electrodes from the current application electrodes 31, 32, . . . 3M, and supplying a current outputted from the voltage-current converter 2; N voltage measurement electrodes 81, 82, . . . 8N, N being 2 or more, placed apart from one another at positions different from the locations of the current application electrodes 31, 32, . . . 3M; an electrode switching unit 9 for selecting an arbitrary pair of voltage measurement electrodes from the N voltage measurement electrodes 81, 82, . . . 8N, and supplying voltage to the selected pair of the electrodes; a measuring unit 4 for measuring a high frequency voltage generated between the two electrodes selected by the electrode switching unit 9 to detect the impedance between two points of the selected electrodes; a retention unit 5 for holding a value of the impedance outputted from the measuring unit 4 for each oscillation frequency; and a computing unit 6 for calculating an impedance difference resulting from different applied oscillation frequencies, based on the impedance values held by the retention unit 5. This underground exploration apparatus can readily change the current path and therefore is capable of proper underground exploration even when an object buried in the ground or soil contamination has directivity or spreads lopsidedly. This means that the apparatus is capable of identifying the location, depth and amount of underground streams and resources or soil contaminants, and substances contained in a geological layer, or measuring or monitoring the progress of soil improvement with precision when the search target has directivity.

According to still another aspect of the present invention, in the underground exploration apparatus, preferably the voltage signal generated by the oscillator 1 is a sine wave, a triangular wave, a saw tooth wave, or a rectangular wave, or one obtained by diphase modulation of the sine wave, triangular wave, saw tooth wave, or rectangular wave with a maximum length binary code sequence of a frequency that corresponds to the quotient of the fundamental oscillation frequency divided by an. integer. This underground exploration apparatus can readily catch a weak electric potential amidst noise at a high S/N ratio without being influenced by an ground feedback component of a current flowing in a power transmission line or the overhead wire of a railway, or by a leak current from an electric appliance, and therefore is capable of highly noise-resistant underground exploration.

Preferably, a long-cycle, M-sequence code is used with a rectangular wave as a maximum length binary code sequence of a frequency that corresponds to the quotient of the fundamental oscillation frequency divided by an integer. The M-sequence code possesses autocorrelation characteristics by which influence of leak current or static electricity (free charge) builds up in the ground can be limited.

According to still another aspect of the present invention, the underground exploration apparatus further includes a mechanism for moving the pair of voltage measurement electrodes 81 and 82 on the ground surface with a distance between the electrodes kept to a fixed value, where measurement is carried out while the voltage measurement electrodes are moved on the ground surface. This underground exploration apparatus, which can keep the distance between the electrodes to a fixed value during measurement, is improved in measurement precision even more and, in addition, only needs markedly a reduced measuring time.

According to yet another aspect of the present invention, in the underground exploration apparatus, preferably the N voltage measurement electrodes 81, 82, . . . 8N are arranged two-dimensionally on the ground surface, and a display unit 11 is provided which displays a two-dimensional map based on data, supplied from the computing unit 6, of the impedance difference resulting from different applied oscillation frequencies. This underground exploration apparatus can provide the same effect as measuring the amplitude of a high frequency voltage that is induced on an electric potential measurement surface when a current flows only in a region where the current path has been changed by a change in applied frequency.

Figure 6A:
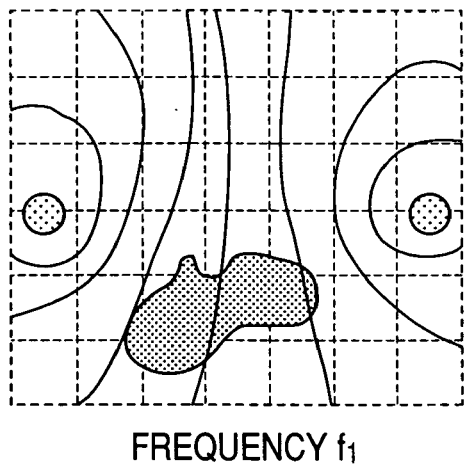
FIGS. 6A, 6B, 6C and 6D are diagrams illustrating the mechanism of processing of the underground exploration apparatus according to an embodiment of the present invention (Embodiment 3)
Figure 6B:
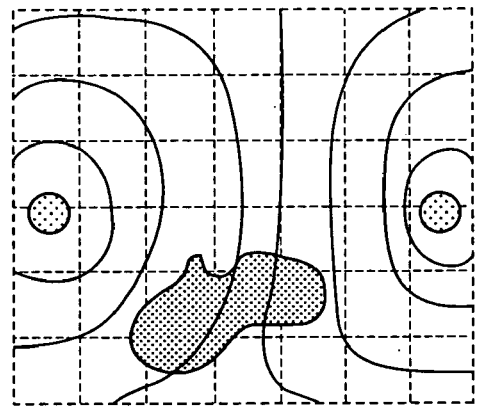
Figure 6C:
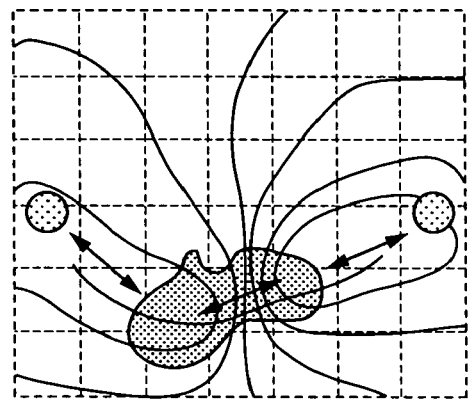

An equivalent circuit model shown in FIG. 5B is established when a region having characteristics of the electric conductivity σ2 and the dielectric constant ∈2 is present in the ground having characteristics of the electric conductivity σ1 and the dielectric constant ∈1, as shown in FIG. 5A. In this case, it can be defined that the ground has a resistor R1 and a capacitor C1, whereas the region has a resistor R2 and a capacitor C2. When the dielectric constant ∈2 is larger than the dielectric constant ∈1 at a frequency f1, the applied current mainly flows in the region at the frequency f1 as shown in FIG. 5C. When the dielectric constant ∈2 of the region markedly drops at a frequency f2 by exceeding the tracking speed, which is one of the factors in polarization, the capacitor C2 is reduced to increase the impedance of the region and stop the concentration of current in the region, as shown in FIG. 5D. Therefore, calculating the difference in impedance measurement value between the both means to obtain the difference resulting from dispersion of the current flowing in the region and, ultimately, to obtain a pattern of electric potential distribution caused by the current flowing concentratedly in the region. This two-dimensional electric potential distribution pattern is highly dipolar and therefore presents a contour map of strongly dipolar property immediately above the region as shown in FIG. 6C when displayed as a two-dimensional map based on the data of the impedance difference. In short, a unique effect is achieved in that a deep region in the ground can be detected by an observation conducted on the ground surface.

According to yet another aspect of the present invention, in the underground exploration apparatus, preferably the N voltage measurement electrodes 81, 82, . . . 8N are arranged two-dimensionally on the ground surface, and a display unit 11 is provided which performs two-dimensional interpolation processing based on data, supplied from the computing unit 6, of the impedance difference resulting from different applied oscillation frequencies, deems the two-dimensional arrangement as a plane with respect to obtained two-dimensional interpolation values axially, and performs differentiation processing in each direction of two axes of x and y on the plane where the axis x and the axis y intersect each other, and displays a two-dimensional vector or arrow map where an x-directional differential value and a y-directional differential value as components of a vector. When there is a region in the ground where current flows concentratedly at one of the frequencies, this underground exploration apparatus can provide a chart that has approximately the same vector as the current flowing in the region through the following steps: obtaining a two-dimensional electric potential map of the ground surface by performing two-dimensional interpolation processing based on the impedance difference data; since the map indicates that sharp fluctuations take place immediately above the current concentration site, deeming the above-mentioned two-dimensional arrangement as a plane, and performing differentiation processing on the obtained two-dimensional interpolation values in each direction of two axes of x and y on the plane where the axis x and the axis y intersect each other; and displaying a two-dimensional vector or arrow map where an x-directional differential value and a y-directional differential value are deemed as components of a vector. In short, this underground exploration apparatus is capable of visualizing a site in which a change in the density of a passing current has occurred in the form of a two-dimensional vector or an arrow map.

Preferably, the vector is obtained by using Expression 1:

$$\left(\frac{\delta E}{\delta y}, \frac{-\delta E}{\delta x}\right) \qquad \text{(Expression 1)}$$

According to still another aspect of the present invention, in the underground exploration apparatus, preferably a processing unit 10 is provided which solves the forward problem of an applied current based on three-dimensional coordinates of the M current application electrodes 31, 32, . . . 3M and the N voltage measurement electrodes 81, 82, . . . 8N, and ground data by using the finite element method or the boundary element method, or by using an impedance network, to obtain a high frequency voltage amplitude value that appears in the voltage measurement electrodes in a ground model, and to estimate a substance in the ground by changing the local dielectric constant and electric conductivity of the ground model so as to make an error between the actual measured value and the calculated value smaller, and that a display unit 11 is provided which performs two-dimensional or three-dimensional display processing upon receiving input information and the results of the estimation processing from the processing unit 10. This underground exploration apparatus can solve the inverse problem using a ground model and the iterative procedure, and therefore it is possible to estimate not only an approximate position on the ground surface of a region but also the depth from the surface, size, geometry, electric conductivity, and dielectric constant of the region.

Since the conductivity and dielectric constant can be estimated to identify a substance in the region, and the underground exploration apparatus of the present invention has features of to measuring or monitoring the status of a water leakage, the location, geometry, depth and amount of underground streams and resources or soil contaminants, and the progress of soil improvement.

Figure 11B:
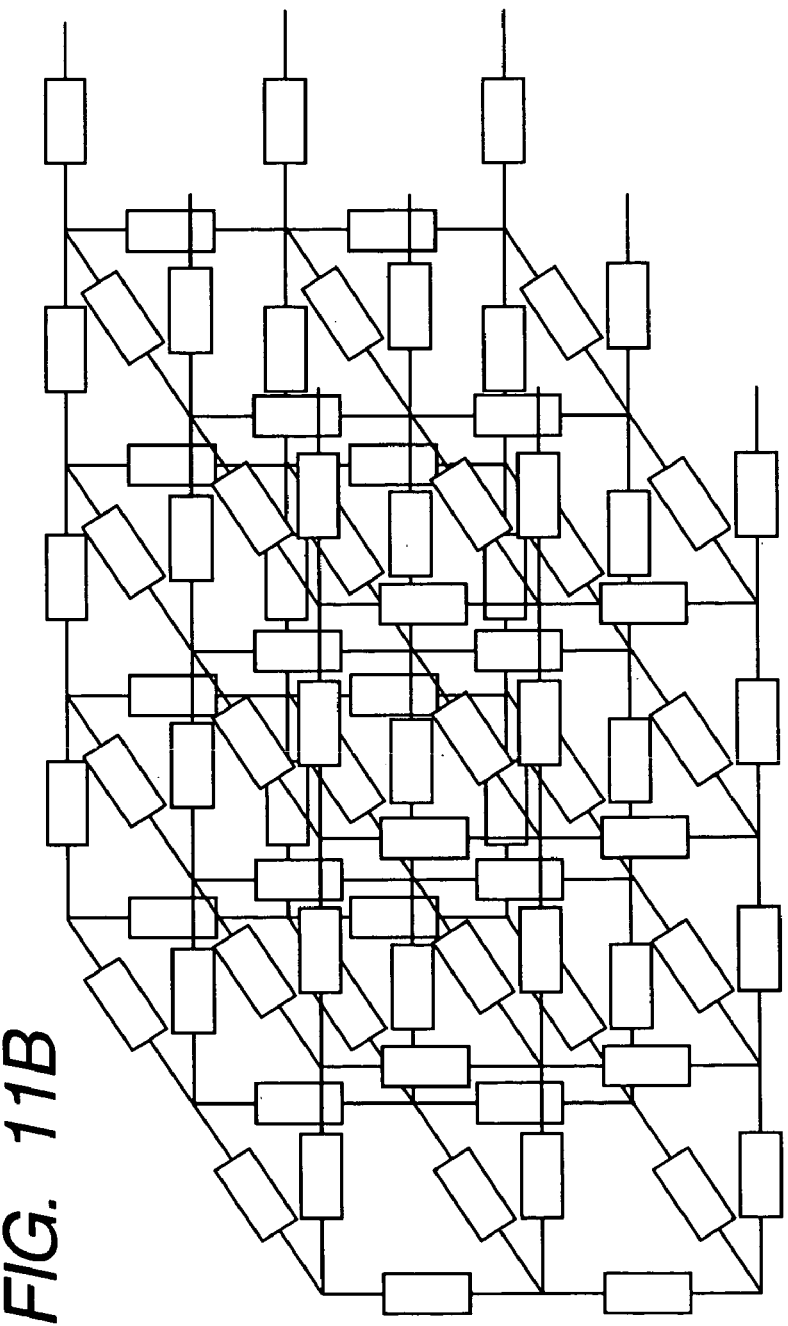
Figure 12B:
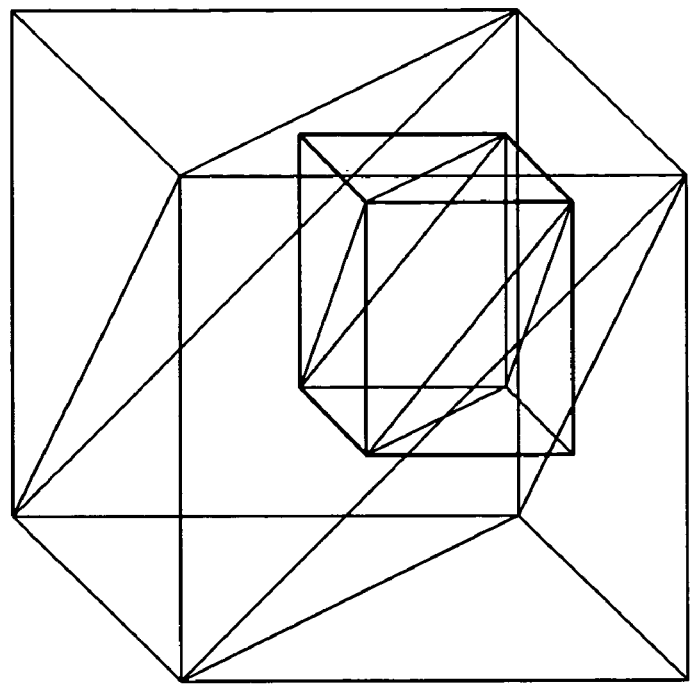
FIGS. 12A and 12B are diagrams illustrating an example of the ground model for an underground exploration apparatus according to an embodiment of the present invention (Embodiment 3)
Figure 12A:
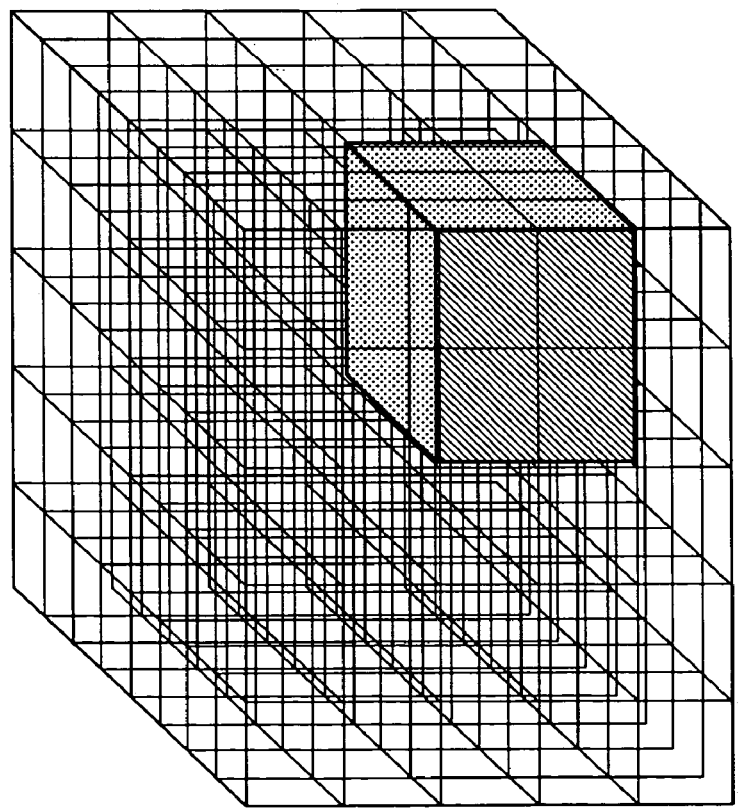

Preferably, an impedance network model that uses an equivalent circuit network such as the one shown in FIGS. 11A and 11B, a finite element method model such as the one shown in FIG. 12A, or a boundary element method model such as the one shown in FIG. 12B is employed as the ground model. This makes it possible to model the region with a small number of parameters and accordingly shorten the computing time for solving the inverse problem significantly.

Embodiments of the present invention will be described in detail below with reference to the drawings. The same or corresponding components in the drawings are denoted by the same numerals and a description thereof will not be repeated.

Embodiment 1

FIG. 2 is a table showing the fact that substances constituting the ground, chemicals, and the like have different specific dielectric constants, which forms the basis of the measurement principle of the present invention. Specific dielectric constant is a coefficient indicating the readiness of the corresponding substance to polarize, in relation to the vacuum dielectric constant. The substance's actual dielectric constant $\epsilon$ can be obtained by multiplying the vacuum dielectric constant by the specific dielectric constant of the substance. The dielectric constant generally fluctuates depending on the frequency and temperature employed in the measurement.

FIG. 3 is a diagram illustrating the frequency dependency of the dielectric constant and fluctuation factors thereof. as mentioned, the dielectric constant is a coefficient indicating the readiness to polarize. There are four known types of polarization of a substance: interface polarization, dipole polarization, ion polarization, and electronic polarization. FIGS. 4A and 4B are diagrams illustrating interface polarization and dipole polarization.

As shown in FIG. 4A, interface polarization is triggered by charged particles present in a gap in a grain boundary being moved by an external electric field. Since interface polarization is a phenomenon that is caused by a slow migration of a substance of large mass, interface polarization takes place at a frequency lower than any other type of polarization. Usually, the interface polarization takes place at a frequency ranging from direct current (DC) to a few kHz. When the applied frequency exceeds a few kHz, the migration speed cannot respond quickly enough for this phenomenon to occur, so that no polarization occurs in this state, and the dielectric constant is lower than at lower frequencies. Interface polarization is also influenced by the size of the gaps in grain boundaries and by the viscosity of charged particles migrating, and is also dependent on temperature. Being dependent on the nature of the soil and the type of charged particles contained therein, therefore, interface polarization provides data for judging the geological condition and substances contained in the ground.

Dipole polarization takes place when an external electric field changes the orientation of polarized molecules that constitute charged particles, as shown in FIG. 4B. Rather than moving charged particles themselves to different locations, in this phenomenon the orientation of charged particles is changed, and this occurs in a shorter time than with interface polarization. The frequency at which response of this type to the applied fiels stops in dipole polarization is 1 MHz to 100 MHz, and therefore is higher than that in the interface polarization. This limit follow-up (response) frequency is determined by molecular weight and the degree of molecular polarization, and thus provides data relevant to the identification of the molecule(s) present.

FIGS. 5A to 5D are diagrams illustrating a measurement principle that is most closely related to the present invention. As shown in FIG. 5A, current application electrodes are placed at two points on the ground, and a high frequency current is applied between the two electrodes. The electric conductivity and dielectric constant of the ground are denoted by $\sigma 1$ and $\epsilon 1$, respectively. A region in the ground has electric properties different from those of surrounding areas, and the electric conductivity and dielectric constant of this region are denoted by $\sigma 2$ and $\epsilon 2$, respectively. Dielectric constant in general is relatively little influenced by frequency. The ground and the region can each be considered as an equivalent circuit in which a resistor and a capacitor are connected in parallel. The resistivity and capacitance of the equivalent circuit that represents the ground are given as R1 and C1, respectively. The resistivity and capacitance of the equivalent circuit that represents the region are given as R2 and C2, respectively.

Assume here that the ground is soil, whereas the region is soil permeated with water. As the table of FIG. 2 shows, the specific resistance of soil is 5 to 40 and the specific resistance of water is about 80. A water molecule is formed with polar covalent bonds between one oxygen atom and two hydrogen atoms, and therefore has only weak polarizability. Six to seven water molecules are linked to one another like a string by their weak polarizability at a temperature of about 20° C. This short chain of linked water molecules also is polarized and exhibits the nature of interface polarization. The region containing water has higher dielectric constant than that of the surrounding ground at a low frequency f1, as shown in FIG. 5C, and the impedance of the region is lower by that much, causing the applied current to flow in the region at a higher density than in the surrounding ground. On the other hand, at a high frequency f2, which exceeds the tracking speed of the interface polarization, the dielectric constant of the region is reduced as the interface polarization ceases to occur. Consequently, the flow of the applied current is made approximately even, as shown in FIG. 5D.

FIG. 7 shows Embodiment 1 of the present invention. Reference numeral 1 denotes an oscillator which generates a signal constituting the base of an applied current. 2 denotes a voltage-current converter for converting a voltage signal into current. 3 denotes current application electrodes. 31, 32, . . . 3M denote current application electrodes. 4 denotes a measuring unit for measuring impedance by synchronous detection in which detection takes place in synch with a signal generated by the oscillator. 5 denotes a retention unit for holding measurement data for each frequency applied. 6 denotes a computing unit for calculating an impedance difference resulting from changing frequencies. 7 denotes a judging unit for judging from the impedance difference whether a sandblast has occurred or not. 81, 82, . . . 8N denote voltage measurement electrodes. 9 denotes an electrode-switching unit for selecting the voltage between arbitrary voltage measurement electrodes. 10 denotes a processing unit for analysis of the inverse problem interpolation processing, and the like, with the use of a ground model. 11 denotes a display unit. 12 denotes a current supply-selecting unit for selecting a current application electrode to change a current supply path. When water leaks rapidly from a water service pipe buried near a gas service pipe to the direction of the gas service pipe, and the gas service pipe is blasted with soil and sand along with the stream of water, the gas service pipe is damaged, allowing water to enter its interior. Such a rapid leakage of water mixed with ground and sand is called a "sandblast". FIG. 7 shows an example of a detection system for detecting at an early stage the sandblast phenomenon, which is often found too late from the ground surface.

In FIG. 7, the oscillator 1 is a high frequency voltage signal emitter capable of selecting two or more oscillation frequencies, and supplying a signal to the voltage-current converter 2 which converts a voltage signal into current. The voltage-current converter supplies a high frequency current to two electrodes 3 buried in the vicinity of a gas service pipe that is a target of early sandblast warning. When there is no water leakage, a substantially uniform current flows between the underground electrodes 3 along the gas service pipe as shown in FIGS. 7 and 8A. A high frequency voltage is generated in the electrodes 3 in accordance with the current flowing between the electrodes 3 and the impedance of the soil between the electrodes. As shown in detail in FIG. 7, the measuring unit 4 is supplied with a high frequency voltage signal for synchronous detection from the oscillator 1, and performs synchronous detection processing by amplifying the voltage induced between the electrodes 3, performing multiplication processing, and passing high frequency ripple components through a low-pass filter. That is, since the measuring unit 4 obtains the amplitude value of the high frequency voltage generated between the electrodes as a result of applying a current at a fixed amplitude, the impedance between the electrodes is measured. By receiving the impedance value from the measuring unit 4, the retention unit 5 keeps in an internal memory the impedance value for each applied frequency. The retention unit 5 supplies measurement data to the computing unit 6, where the impedance difference (change value) resulting from changing applied frequencies is calculated and supplied to the judging unit 7. The judging unit 7 judges whether or not a change in impedance that is larger than a preset amount has taken place in a short time, thereby detecting at an early stage a water leakage from the water service pipe buried near the gas service pipe and the impending occurrence of the sandblast phenomenon.

The operation of this embodiment will be described in more detail. FIG. 8B is a diagram illustrating a rapid water leakage taking place in a water service pipe buried in the vicinity of a gas service pipe. As shown in FIG. 8B, a current applied to the electrodes 3 tends to be pulled toward the water leakage site which is a region having a low impedance. Since the applied current flows along the gas service pipe, the current is more strongly pulled as the water leakage site becomes larger and approaches the gas service pipe. FIG. 8C is a diagram showing the contour lines of the current density as seen in a cross-section of the gas service pipe. In the case where the impedance is sharply dropped at the low frequency f1, the impedance at the high frequency f2 is also measured to obtain the difference in impedance from which occurrence of the sandblast phenomenon is detected. This embodiment is capable of precisely detecting only a serious water leakage which could develop into the sandblast phenomenon and damage a gas service pipe among water leakages that takes place near the gas service pipe.

Embodiment 2

Figure 9:
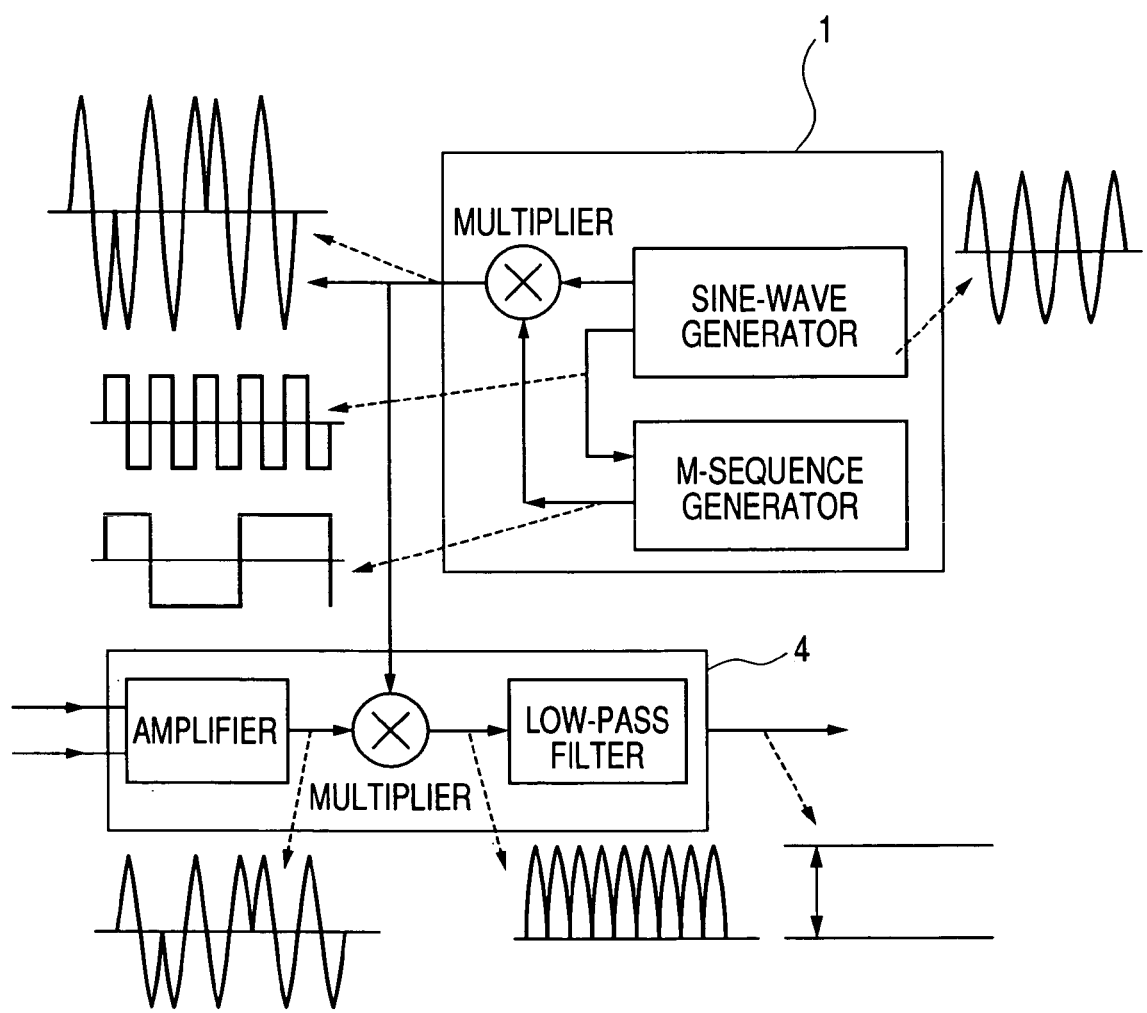
FIG. 9 is a diagram illustrating the structure of an oscillator 1 of an underground exploration apparatus according to an embodiment of the present invention (Embodiment 2)

FIG. 9 is a diagram illustrating a detailed structure of an oscillator 1 according to another embodiment of the present invention. There are various electric currents flowing under the ground that can be disturbances to AC tests. Such electric currents include those accompanying movement of static electricity build-up in the ground, or flowing back from a power transmission line or the overhead wire of a railway through the ground, or leaking from an electric appliance, and the like. In order to detect a minuscule change in impedance without being influenced by those currents, it is preferable to use an oscillator structured as shown in FIG. 9.

A sine-wave generator shown in FIG. 9 generates a sine wave to supply the signal to a multiplier and, in addition, supplies a clock signal to an M-sequence generator in sync with a fundamental frequency. The M-sequence generator is an electronic circuit for generating a maximum length code sequence ("M-sequence code"), which is a binary code having the longest cycle in a binary code generator that can be constituted of L levels of registers. The maximal code length that can be generated by using L levels of registers is the L-th power of 2 minus 1 ($2^L-1$) bits. M-sequence code is also called as pseudo-noise and has strong autocorrelation. The nature of M-sequence code is such that $(+1)\times(+1)=1$ and $(-1)\times(-1)=1$ when +1 is to be generated corresponding to the "H" state of binary logic, whereas −1 is to be generated corresponding to the "L" state and when multiplied by 0 phase of the same sign.

Accordingly, a high frequency voltage, which is generated as a result of application of a current signal obtained by multiplying a sine wave by an M-sequence and performing diphase modulation, is a signal of the same phase or reverse phase of an applied sine wave which is subjected to diphase modulation with an M-sequence. Therefore, decoding equal to synchronous detection is achieved by multiplying the transmitted wave once more. However, even when a direct or alternating disturbance current is superimposed on the received high frequency signal, the signal has no correlation with the transmitted wave modulated by pseudo-noise. The disturbance current components are therefore diffused by the pseudo-noise and, when correlation values corresponding to one cycle of the M-sequence are taken, the signal size becomes what corresponds to one part of the strength of the unadulterated signal equally divided by the code length. In short, current noise irrelevant to the measurement can be reduced by using a M-sequence code that has a sufficiently long code length.

The structure described above makes it possible to measure impedance with very high precision in underground exploration without being influenced by disturbance current in the ground even when there is a considerably large environmental current noise, and accordingly to obtain an impedance difference accompanying a minuscule change in dielectric constant.

Embodiment 3

FIG. 1 is a diagram showing the structure of an underground exploration apparatus according to a still another embodiment of the present invention. In FIG. 1, a transmitter waveform generated by the oscillator 1 is converted into current by the voltage-current converter 2 and then conducted to the ground via the ends of the pair of current application electrodes 3. As a result of the current conduction, a high frequency voltage generated between two arbitrary electrodes chosen out of the N voltage measurement electrodes 81, 82, 83, 84, . . . , 8N, which are provided to measure a high frequency voltage induced on the ground surface, is supplied to an amplifier via the electrode switching unit 9. The high frequency voltage is multiplied in sync with the transmitted wave, and is passed through a low-pass filter for synchronous detection processing. The measuring unit 4 composed of the amplifier, the multiplier, and the low-pass filter serves as a synchronous detection circuit. An output signal of the measuring unit is in proportion to impedance since the current amplitude of the transmitted wave is a fixed value. The output of the measuring unit 4 is kept by the retention unit 5 for each measurement frequency, so that the computing unit 6 can calculate an impedance difference resulting from changing applied frequencies and supply the calculation result to the processing unit 10. The processing unit 10 performs a plurality of information processings based on the impedance difference which is measurement data. Then, if necessary, the display unit 11 performs two-dimensional or three-dimensional display processing.

Now a description is given on processing performed in the processing unit 10. FIGS. 6A and 6B are obtained by calculating two-dimensional interpolation values of measured values based on the difference between impedance values measured at one frequency level and the impedance measured at two or more frequencies on the assumption that the surface on which the electric potential measurement electrodes are arranged is a flat surface. Calculating the difference between the thus obtained FIGS. 6A and 6B has the following meaning. The difference between the impedance distribution measured at the frequency f1 and the impedance distribution measured at the frequency f2 is equal to the result of the above processing, and this provides a pattern of electric potentials generated when a current having the same density as the changed current density only in the region where the current has been changed by a change in frequency. A contour map of FIG. 6C is the pattern of electric potentials expected to be generated due to the above differential current, and therefore appears as a dipole pattern immediately above the region that has undergone a great change in dielectric constant as a result of changing frequencies.

Figure 6D:
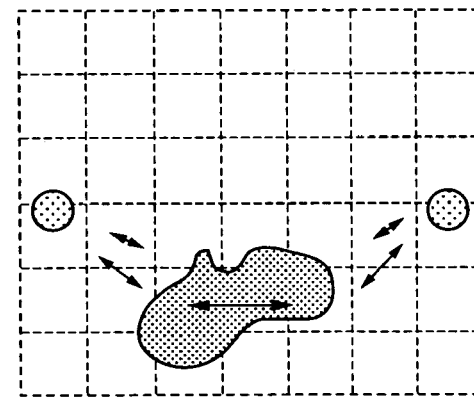

Information processing as defined by Expression 1 is performed on the two-dimensional interpolation values to obtain a two-dimensional diagram having a vector approximately matching the current conduction direction immediately above the region where the dielectric constant has been changed greatly, as shown in FIG. 6D. The diagram can be displayed on the display unit 11.

The processing described above facilitates identification of the position immediately above a region that has a different dielectric constant.

The processing unit 10 can also solve the inverse problem for estimating unknown quantities, namely, electric conductivity, dielectric constant, three-dimensional coordinates, size, and geometry, by using as a ground model the impedance network shown in FIGS. 11A and 11B, the finite element model shown in FIG. 12A, or the boundary element model shown in FIG. 12B and by using iterative procedure in a manner that makes an error between the actually measured value and the calculated value according to the ground model smaller.

Tomoaki Ueda, one of the inventors of the present invention, has described a processing method of estimating an unknown quantity using a boundary element method model and the iterative procedure in an article titled "Attempt to Estimate Conductivity of Living Tissue for Inverse Problem Analysis", which is found on pages 7 to 13 of Journal No. 2 of the Japan Biomagnetism and Bioelectromagnetics Society, published in 1995.

The above structure makes it possible to estimate unknown quantities about a deep region in the ground using a ground model. Therefore, geological substances and substances contained in the ground can be identified from information of frequencies used in the measurement and information of the electric conductivity and dielectric constant estimated.

Embodiment 4

Figure 10:
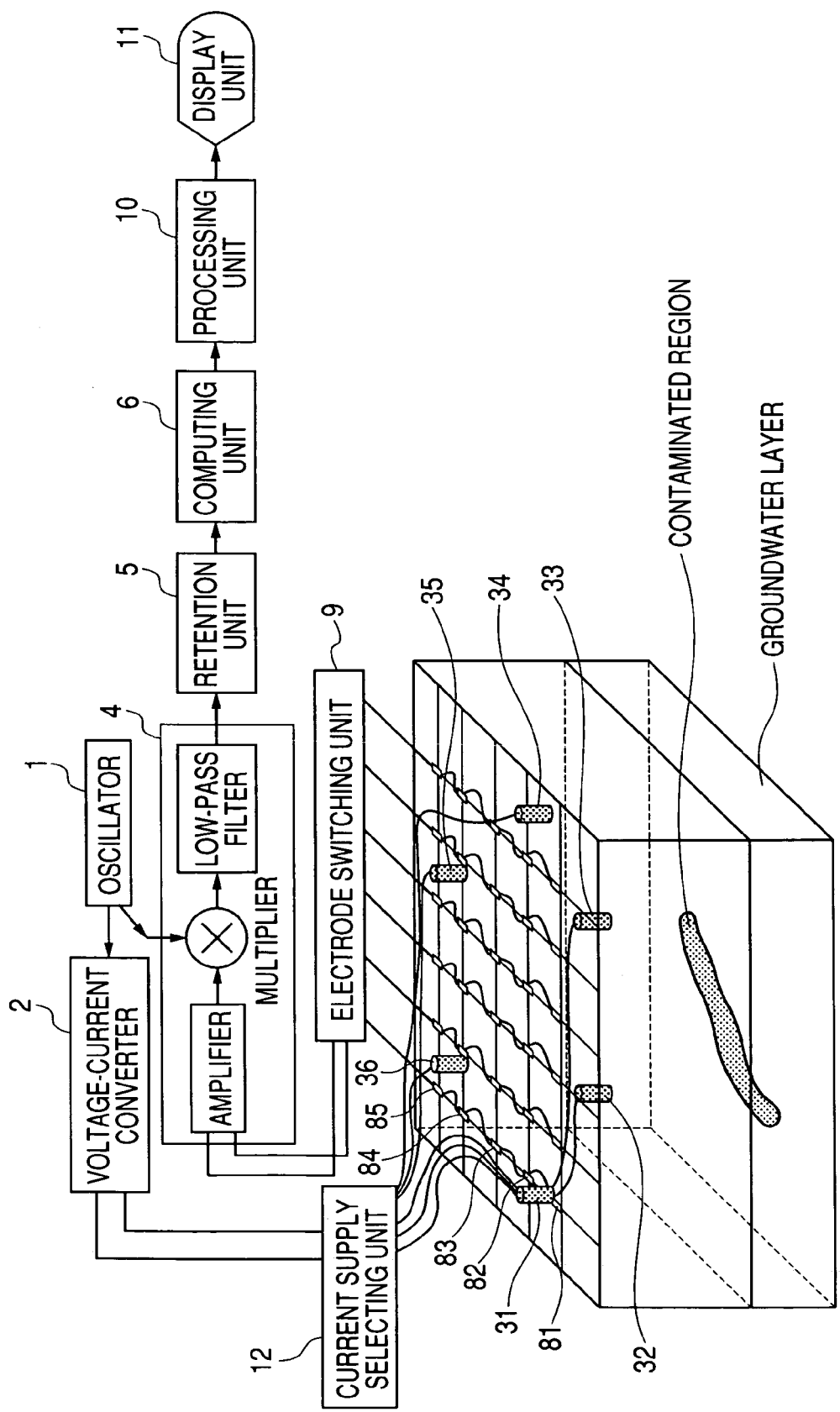
FIG. 10 is a diagram illustrating the structure of an underground exploration apparatus according to an embodiment of the present invention (Embodiment 4)

FIG. 10 is a diagram showing the structure of an underground exploration apparatus according to yet still another embodiment of the present invention. The differences from FIG. 1 are to arrange three or more current application electrodes and to provide a current supply-selecting unit 12 for selecting current application electrodes for supplying a current.

The above structure can freely change the current conduction direction, and therefore is capable of detecting with precision a region that has a different geological condition, estimating unknown quantities of the region, and specifying the region's geological condition and substances contained in the region even when the region spreads with directivity.

The embodiments disclosed herein should be understood in every way as exemplifications, and are not restrictive. The scope of the present invention is determined not by the description given above but by the following claims. It is intended that any modification within the spirit and scope of the claims and equivalent to the claims is include within the scope of the present invention.

Effect of the Invention

As described above, the present invention provides a specific effect of finding out the geological condition and substances contained therein accurately without being influenced by background current noise, by conducting an underground exploration using an only slightly invasive AC test.

Another specific effect of the present invention is to detect at an early stage the sandblast phenomenon induced by leakage of water from a water service pipe buried near a gas service pipe, which could cause serious damage to the gas service pipe.

Still another specific effect of the present invention is to specify the location, depth, and amount of underground streams and resources or soil contaminants, and substances contained in a geological layer, or to measure or monitor the progress of soil improvement by the unknown quantity estimation processing using a ground model.

Yet still another specific effect of the present invention is easily to identify an approximate location of a buried contaminant or resource by using a vector diagram or arrow map based on a two-dimensional distribution map that is subjected to interpolation processing on the assumption that the ground surface on which electric potential measurement electrodes are arranged is a flat surface.

What is claimed is:

1. An underground exploration apparatus comprising:
an oscillator capable of selecting among two or more fundamental oscillation frequencies;
a voltage-current converter for converting a voltage signal generated by the oscillator into current;

a pair of electrodes placed on or buried in the ground apart from each other in order to conduct a high frequency current supplied by the voltage-current converter through the ground;

a measuring unit for measuring a high frequency voltage generated between both ends of the electrodes to detect an impedance between two points of the electrodes;

a retention unit for holding a value of the impedance outputted from the measuring unit for each oscillation frequency;

a computing unit for calculating a difference between impedances held by the retention unit to obtain an impedance difference resulting from different oscillation frequencies; and a judging unit for detecting and judging a large change in impedance between the two points of the electrodes within a short time by at least one of the frequencies, based on the impedance difference calculated by the computing unit.

2. An underground exploration apparatus according to claim 1, wherein the voltage signal generated by the oscillator is a sine wave, a triangular wave, a saw tooth wave, or a rectangular wave, or one obtained by diphase modulation of the sine wave, the triangular wave, the saw tooth wave, or the rectangular wave with a maximum length binary code sequence of a frequency that corresponds to a quotient of the fundamental oscillation frequency divided by an integer.

3. An underground exploration apparatus comprising:

an oscillator capable of selecting among two or more fundamental oscillation frequencies;

a voltage-current converter for converting a voltage signal generated by the oscillator into current;

a pair of current application electrodes placed on or buried in the ground apart from each other in order to conduct a high frequency current supplied by the voltage-current converter through the ground;

a pair of voltage measurement electrodes placed apart from each other at positions different from locations where the current application electrodes are set;

a measuring unit for measuring a high frequency voltage generated between the two voltage measurement electrodes to detect an impedance between two points of the voltage measurement electrodes;

a retention unit for holding a value of the impedance outputted from the measuring unit for each oscillation frequency; and a computing unit for calculating an impedance difference resulting from different applied oscillation frequencies, based on the impedance value held by the retention unit.

4. An underground exploration apparatus according to claim 3, further comprising a mechanism for moving the pair of voltage measurement electrodes on a ground surface with a distance between the electrodes kept to a fixed value, wherein measurement is carried out while the voltage measurement electrodes are moved on the ground surface.

5. An underground exploration apparatus comprising:

an oscillator capable of selecting among two or more fundamental oscillation frequencies;

a voltage-current converter for converting a voltage signal generated by the oscillator into current;

a pair of current application electrodes placed on or buried in the ground apart from each other in order to conduct a high frequency current supplied by the voltage-current converter through the ground;

N voltage measurement electrodes, N being 2 or more, placed apart from one another at positions different from locations where the current application electrodes are set;

an electrode switching unit for selecting an arbitrary pair of voltage measurement electrodes from the N voltage measurement electrodes and supplying voltage to the selected pair of the electrodes;

a measuring unit for measuring a high frequency voltage generated between the two electrodes selected by the electrode switching unit to detect an impedance between two points of the selected electrodes;

a retention unit for holding a value of the impedance outputted from the measuring unit for each oscillation frequency; and a computing unit for calculating an impedance difference resulting from different applied oscillation frequencies, based on the impedance value held by the retention unit.

6. An underground exploration apparatus according to claim 5, wherein the N voltage measurement electrodes are arranged two-dimensionally on a ground surface, and a display unit is provided which displays two-dimensional map based on data, supplied from the computing unit, of the impedance difference resulting from the different applied oscillation frequencies.

7. An underground exploration apparatus according to claim 6, wherein a processing unit is provided which solves a forward problem of an applied current based on three-dimensional coordinates of the current application electrodes and the voltage measurement electrodes, and ground data by using a finite element method or a boundary element method, or by using an impedance network, to obtain as a calculated value a high frequency voltage amplitude value that appears in the voltage measurement electrodes in an ground model, and to estimate a substance in the ground by changing a local dielectric constant and an electric conductivity of the ground model so as to make an error between the calculated value and an actual value thereof smaller, and that a display unit is provided which performs two-dimensional or three-dimensional display processing upon receiving input information and results of the estimation processing from the processing unit.

8. An underground exploration apparatus according to claim 5, wherein the N voltage measurement electrodes are arranged two-dimensionally on a ground surface, and wherein a display unit is provided which performs two-dimensional interpolation processing based on data supplied, from the computing unit, of the impedance difference resulting from the different applied oscillation frequencies; deems the two-dimensional arrangement as a plane with respect to obtained two-dimensional interpolation values, and performs differentiation processing in each direction of two axes of x and y on the plane where the axis x and the axis y intersect each other; and displays a two-dimensional vector or arrow map obtained by deeming an x-directional differential value and a y-directional differential value as components of a vector.

9. An underground exploration apparatus comprising:

an oscillator capable of selecting among two or more fundamental oscillation frequencies;

a voltage-current converter for converting a voltage signal generated by the oscillator into current;

M current application electrodes, M being 2 or more, placed on or buried in the ground apart from one another in order to conduct a high frequency current through the ground;

a current supply selecting unit for selecting an arbitrary pair of current application electrodes from the current application electrodes, and supplying a current outputted from the voltage-current converter to the selected pair of the electrodes;

N voltage measurement electrodes, N being 2 or more, placed apart from one another at positions different from locations where the current application electrodes are set;

an electrode switching unit for selecting an arbitrary pair of voltage measurement electrodes from the N voltage measurement electrodes, and supplying voltage to the selected pair of the electrodes;

a measuring unit for measuring a high frequency voltage generated between the two electrodes selected by the electrode switching unit to detect an impedance between two points of the selected electrodes;

a retention unit for holding a value of the impedance outputted from the measuring unit for each oscillation frequency; and a computing unit for calculating an impedance difference resulting from different applied oscillation frequencies, based on the impedance values held by the retention unit.

10. An underground exploration system comprising:
an oscillator capable of selecting among two or more fundamental oscillation frequencies;
a voltage-current converter for converting a voltage signal generated by the oscillator into current;
a pair of electrodes placed on or buried in the ground apart from each other in order to conduct a current supplied by the voltage-current converter through the ground;
a measuring unit for measuring a voltage generated between both ends of the electrodes to detect an impedance between two points of the electrodes;
a retention unit for holding a value of the impedance outputted from the measuring unit for each oscillation frequency;
a computing unit for calculating a difference between impedances held by the retention unit to obtain an impedance difference resulting from different oscillation frequencies; and
a judging unit for detecting and judging a large change in impedance between the two points of the electrodes within a short by at least one of the frequencies, based on the impedance difference calculated by the computing unit.

11. An underground exploration system comprising:
an oscillator capable of selecting among two or more fundamental oscillation frequencies;
a voltage-current converter for converting a voltage signal generated by the oscillator into current;
a pair of current application electrodes placed on or buried in the ground apart from each other in order to conduct a current supplied by the voltage-current converter through the ground;
a pair of voltage measurement electrodes placed apart from each other at positions different from locations where the current application electrodes are set;
a measuring unit for measuring a voltage generated between the two voltage measurement electrodes to detect an impedance between two points of the electrodes;
a retention unit for holding a value of the impedance outputted from the measuring unit for each oscillation frequency; and
a computing unit for calculating an impedance difference resulting from different applied oscillation frequencies, based on the impedance value held by the retention unit.

12. An underground exploration system comprising:
an oscillator capable of selecting among two or more fundamental oscillation frequencies;
a voltage-current converter for converting a voltage signal generated by the oscillator into current;
a pair of current application electrodes placed on or buried in the ground apart from each other in order to conduct a current supplied by the voltage-current converter through the ground;
N voltage measurement electrodes, N being 2 or more, placed apart from one another at positions different from locations where the current application electrodes are set;
an electrode switching unit for selecting an arbitrary pair of electrodes from the N voltage measurement electrodes and supplying voltage to the selected pair of the electrodes;
a measuring unit for measuring a voltage generated between the two electrodes selected by the electrode switching unit to detect an impedance between two points of the selected electrodes;
a retention unit for holding a value of the impedance outputted from the measuring unit for each oscillation frequency; and
a computing unit for calculating an impedance difference resulting from different applied oscillation frequencies, based on the impedance value held by the retention unit.

13. An underground exploration system comprising:
an oscillator capable of selecting among two or more fundamental oscillation frequencies;
a voltage-current converter for converting a voltage signal generated by the oscillator into current;
M current application electrodes, M being 2 or more, placed on or buried in the ground apart from one another in order to conduct a current through the ground;
a current supply selecting unit for selecting an arbitrary pair of electrodes from the current application electrodes and supplying a current outputted from the voltage-current converter to the selected pair of the electrodes;
N voltage measurement electrodes, N being 2 or more, placed apart from one another at positions different from locations where the current application electrodes are set;
an electrode switching unit for selecting an arbitrary pair of voltage measurement electrodes from the N voltage measurement electrodes and supplying voltage to the selected pair of the electrodes;
a measuring unit for measuring a voltage generated between the two electrodes selected by the electrode switching unit to detect an impedance between two points of the selected electrodes;
a retention unit for holding a value of the impedance outputted from the measuring unit for each oscillation frequency; and
a computing unit for calculating an impedance difference resulting from different applied oscillation frequencies, based on the impedance value held by the retention unit.

14. An underground exploration method comprising:

a step of conducting a current of two or more different oscillation frequencies through a pair of current application electrodes placed on or buried in the ground apart from each other, or an arbitrary pair of current application electrodes selected from a plurality of current application electrodes placed on or buried in the ground apart from one another;

a step of measuring a voltage generated between a pair of voltage measurement electrodes placed on the ground apart from each other, or between an arbitrary pair of voltage measurement electrodes selected from a plurality of voltage measurement electrodes placed on the ground apart from one another to detect an impedance value between two points of the pair of voltage measurement electrodes;

a step of holding the impedance value for each oscillation frequency; and a step of calculating a difference in the impedance value to obtain an impedance difference resulting from different oscillation frequencies.

15. An underground exploration method according to claim 14, further comprising a step of detecting and judging that the impedance difference is changed.

\* \* \* \* \*

UNITED STATES PATENT AND TRADEMARK OFFICE
CERTIFICATE OF CORRECTION

| | |
|---|---|
| PATENT NO. | : 7,034,539 B2 |
| APPLICATION NO. | : 10/991404 |
| DATED | : April 25, 2006 |
| INVENTOR(S) | : Tomoaki Ueda et al. |

It is certified that error appears in the above-identified patent and that said Letters Patent is hereby corrected as shown below:

ON THE TITLE PAGE ITEM [57] ABSTRACT:

Line 9, "an" should read --a--.

COLUMN 1:

Line 21, "an" should read --a--.

COLUMN 2:

Line 30, "prevent" should read --prevents--; and Line 36, "therefor" should read --therefore--.

COLUMN 3:

Line 15, "NIOPPN" should read --NIPPON--; and
Line 50, "side" should read --sides--.

COLUMN 6:

Line 31, "selecting," should read --selecting--; and
Line 64, "two-dimensional" should read --a two-dimensional--.

COLUMN 9:

Line 54, "(Embodiment 3);" should read --(Embodiment 3); and--.

COLUMN 10:

Line 2, "conductivity a" should read --conductivity $\sigma$--.

COLUMN 11:

Line 41, "carry" should read --carrying--.

COLUMN 12:

Line 65, "an." should read --a--.

UNITED STATES PATENT AND TRADEMARK OFFICE
CERTIFICATE OF CORRECTION

PATENT NO. : 7,034,539 B2
APPLICATION NO. : 10/991404
DATED : April 25, 2006
INVENTOR(S) : Tomoaki Ueda et al.

It is certified that error appears in the above-identified patent and that said Letters Patent is hereby corrected as shown below:

COLUMN 14:

Line 67, "of" should be deleted.

COLUMN 15:

Line 34, "as" should read --As--; and
    Line 67, "fiels" should read --field--.

COLUMN 20:

Line 32, "include" should read --included--.

COLUMN 22:

Line 23, "two-dimensional" should read --a two-dimensional--; and
    Line 35, "an" should rend --a--.

Signed and Sealed this

Fifth Day of December, 2006

JON W. DUDAS
*Director of the United States Patent and Trademark Office*